US012588991B2

(12) United States Patent
Schwarcz et al.

(10) Patent No.: US 12,588,991 B2
(45) Date of Patent: Mar. 31, 2026

(54) APPARATUS AND METHOD FOR MONITORING VALVE EXPANSION

(71) Applicant: Edwards Lifesciences Corporation, Irvine, CA (US)

(72) Inventors: Elazar Levi Schwarcz, Netanya (IL); Oren Cohen, Kadima (IL); Ofir Witzman, Harish (IL)

(73) Assignee: Edwards Lifesciences Corporation, Irvine, CA (US)

( * ) Notice: Subject to any disclaimer, the term of this patent is extended or adjusted under 35 U.S.C. 154(b) by 759 days.

(21) Appl. No.: 17/888,348

(22) Filed: Aug. 15, 2022

(65) Prior Publication Data

US 2022/0387174 A1    Dec. 8, 2022

Related U.S. Application Data

(63) Continuation of application No. PCT/US2021/018450, filed on Feb. 18, 2021.

(60) Provisional application No. 62/978,193, filed on Feb. 18, 2020.

(51) Int. Cl.
A61F 2/24 (2006.01)

(52) U.S. Cl.
CPC ...... A61F 2/243 (2013.01); *A61F 2250/0098* (2013.01)

(58) Field of Classification Search
CPC . A61F 2/2439; A61F 2/243; A61F 2002/9511
See application file for complete search history.

(56) References Cited

U.S. PATENT DOCUMENTS

| | | | |
|---|---|---|---|
| 43,882 | A | 8/1864 | Marshall et al. |
| 519,297 | A | 5/1894 | Wanek et al. |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |
| 5,411,552 | A | 5/1995 | Andersen et al. |
| 5,554,185 | A | 9/1996 | Block et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Alvin J Stewart
(74) *Attorney, Agent, or Firm* — Klarquist Sparkman, LLP

(57) ABSTRACT

Embodiments of a prosthetic valve delivery apparatus are disclosed. The delivery apparatus can include an indicator arm changeable between a first configuration and a second configuration. The second configuration is different from the first configuration in location or shape of the indicator arm. The indicator arm can be configured to remain in the first configuration when a diameter of the prosthetic valve is smaller than a first predetermined size, and change to the second configuration when the diameter of the prosthetic valve is expanded to the first predetermined size.

18 Claims, 9 Drawing Sheets

(56) References Cited

U.S. PATENT DOCUMENTS

| | | | |
|---|---|---|---|
| 5,591,195 A | 1/1997 | Taheri et al. | |
| 5,599,305 A | 2/1997 | Hermann et al. | |
| 5,632,760 A | 5/1997 | Sheiban et al. | |
| 5,639,274 A | 6/1997 | Fischell et al. | |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 * | 9/2009 | Linder | A61F 2/95 623/1.11 |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 8,029,556 B2 | 10/2011 | Rowe | |
| 8,167,932 B2 | 5/2012 | Bourang et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 9,061,119 B2 | 6/2015 | Le et al. | |
| 9,119,716 B2 | 9/2015 | Lee et al. | |
| 9,795,477 B2 | 10/2017 | Tran et al. | |
| 10,500,047 B2 * | 12/2019 | Olson | A61F 2/2433 |
| 11,273,038 B2 | 3/2022 | Tang et al. | |
| 2001/0002445 A1 | 5/2001 | Vesely | |
| 2001/0007082 A1 | 7/2001 | Dusbabek et al. | |

| | | | |
|---|---|---|---|
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 * | 3/2003 | Yang | A61F 2/243 623/2.11 |
| 2003/0120341 A1 | 6/2003 | Shennib et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Azizi | |
| 2006/0025857 A1 | 2/2006 | Bergheim et al. | |
| 2006/0282150 A1 | 12/2006 | Olson et al. | |
| 2007/0005131 A1 | 1/2007 | Taylor | |
| 2007/0073389 A1 | 3/2007 | Bolduc et al. | |
| 2007/0088431 A1 * | 4/2007 | Bourang | A61F 2/2436 623/2.11 |
| 2007/0100356 A1 | 5/2007 | Lucatero et al. | |
| 2007/0112422 A1 | 5/2007 | Dehdashtian | |
| 2007/0203503 A1 * | 8/2007 | Salahieh | A61F 2/2436 623/2.11 |
| 2007/0203575 A1 | 8/2007 | Forster et al. | |
| 2007/0219612 A1 | 9/2007 | Andreas et al. | |
| 2007/0233223 A1 * | 10/2007 | Styrc | A61F 2/95 606/108 |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0103520 A1 | 5/2008 | Selkee | |
| 2008/0125853 A1 | 5/2008 | Bailey et al. | |
| 2008/0294230 A1 | 11/2008 | Parker | |
| 2009/0024428 A1 | 1/2009 | Hudock | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0276040 A1 | 11/2009 | Rowe et al. | |
| 2009/0281619 A1 | 11/2009 | Le et al. | |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 * | 2/2010 | Alon | A61F 2/2418 623/2.11 |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0161036 A1 | 6/2010 | Pintor et al. | |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2011/0015729 A1 | 1/2011 | Jimenez et al. | |
| 2011/0054596 A1 | 3/2011 | Taylor | |
| 2011/0137331 A1 | 6/2011 | Walsh et al. | |
| 2011/0160846 A1 | 6/2011 | Bishop et al. | |
| 2012/0123529 A1 | 5/2012 | Levi et al. | |
| 2012/0239142 A1 * | 9/2012 | Liu | A61F 2/2439 623/2.11 |
| 2013/0030519 A1 | 1/2013 | Tran et al. | |
| 2013/0317598 A1 | 11/2013 | Rowe et al. | |
| 2014/0296962 A1 * | 10/2014 | Cartledge | A61F 2/95 623/1.11 |

(56)             References Cited

U.S. PATENT DOCUMENTS

| | | | |
|---|---|---|---|
| 2014/0343670 A1* | 11/2014 | Bakis | A61F 2/2436 |
| | | | 623/2.11 |
| 2015/0157455 A1* | 6/2015 | Hoang | A61M 25/0662 |
| | | | 264/269 |
| 2017/0065415 A1 | 3/2017 | Rupp et al. | |
| 2017/0231765 A1* | 8/2017 | Desrosiers | A61F 2/2418 |
| | | | 623/2.11 |
| 2017/0258587 A1* | 9/2017 | Gloss | A61F 2/2418 |
| 2018/0153689 A1 | 6/2018 | Maimon et al. | |
| 2018/0153693 A1 | 6/2018 | Copeland et al. | |
| 2018/0228607 A1* | 8/2018 | Alon | A61F 2/2436 |
| 2018/0318076 A1* | 11/2018 | Anderson | A61F 2/2439 |
| 2018/0344456 A1 | 12/2018 | Barash et al. | |
| 2019/0231520 A1* | 8/2019 | Desrosiers | A61F 2/2418 |
| 2019/0231566 A1* | 8/2019 | Tassoni | A61B 17/12022 |
| 2022/0160529 A1* | 5/2022 | Arbefeuille | A61F 2/962 |
| 2022/0192822 A1* | 6/2022 | McLean | A61F 2/2439 |
| 2022/0257379 A1* | 8/2022 | Dvorsky | A61F 2/95 |
| 2022/0296369 A1* | 9/2022 | Kheradvar | A61F 2/2427 |
| 2023/0263631 A1* | 8/2023 | Ratz | A61F 2/2436 |
| | | | 623/2.11 |
| 2023/0346582 A1* | 11/2023 | Naveh | A61F 2/966 |

FOREIGN PATENT DOCUMENTS

| | | | |
|---|---|---|---|
| EP | 0592410 | B1 | 10/1995 |
| EP | 0850607 | A1 | 7/1998 |
| FR | 2815844 | A1 | 5/2002 |
| WO | 1991017720 | A1 | 11/1991 |
| WO | 1998029057 | A1 | 7/1998 |
| WO | 1999012483 | A1 | 3/1999 |
| WO | 2001049213 | A2 | 7/2001 |
| WO | 2001054625 | A1 | 8/2001 |
| WO | 2001076510 | A2 | 10/2001 |
| WO | 2002022054 | A1 | 3/2002 |
| WO | 2002036048 | A1 | 5/2002 |
| WO | 2002047575 | A2 | 6/2002 |
| WO | 2002060352 | A1 | 8/2002 |
| WO | 2003030776 | A2 | 4/2003 |
| WO | 2003047468 | A2 | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |

* cited by examiner

APPARATUS AND METHOD FOR MONITORING VALVE EXPANSION

CROSS-REFERENCE TO RELATED APPLICATION

This application is a continuation of PCT Application No. PCT/US2021/018450, entitled "APPARATUS AND METHOD FOR MONITORING VALVE EXPANSION," filed Feb. 18, 2021, which claims the benefit of U.S. Provisional Application No. 62/978,193, entitled "APPARATUS AND METHOD FOR MONITORING VALVE EXPANSION," filed Feb. 18, 2020, where each of above-referenced applications is incorporated herein by reference.

FIELD

The present disclosure concerns embodiments of a systems and methods for monitoring radial expansion of a prosthetic valve.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Because of the drawbacks associated with conventional open-heart surgery, percutaneous and minimally-invasive surgical approaches are garnering attention. In one technique, a prosthetic device is configured to be implanted in a less invasive procedure by way of catheterization. For example, a collapsible transcatheter prosthetic heart valve can be crimped to a compressed state and percutaneously introduced in the compressed state on a catheter and expanded to a functional size at the desired position. Despite the recent advancements in percutaneous valve technology, there remains a need for improved transcatheter heart valves and delivery devices for such valves.

SUMMARY

The present disclosure is directed toward methods and apparatuses relating to monitoring radial expansion of a prosthetic valve, and therefore the size of the prosthetic valve, inside a patient's body. The present disclose is also directed toward methods and apparatuses related to locking the prosthetic valve in a desired expanded diameter.

Certain embodiments of the disclosure concern a delivery apparatus configured to provide visual feedback of the radial expansion of a prosthetic valve. In one representative embodiment, the delivery apparatus includes a first portion and a second portion. The first portion is configured to maintain a fixed spatial relationship relative to a first end of the prosthetic valve, and the second portion is configured to maintain a fixed spatial relationship relative to a second end of the prosthetic valve during radial expansion of the prosthetic valve. The first portion can include one or more reference radiopaque markers and the second portion can include an indicator radiopaque marker. A position of the indicator radiopaque marker relative to the one or more reference radiopaque markers can measure an axial distance between the first and second ends of the prosthetic valve indicative of a corresponding diameter of the prosthetic valve as it is radially expanded from a radially compressed state to a radially expanded state.

Certain embodiments of the disclosure concern also concern a prosthetic valve delivery assembly. The assembly can include a prosthetic valve having an inflow end and an outflow end, and a delivery apparatus having a first portion and a second portion. The second portion can be configured to move axially relative to the first portion as the prosthetic valve is radially expanded from a radially compressed state to a radially expanded state. The first portion can include one or more reference radiopaque marker and the second portion can include an indicator radiopaque marker. A position of the indicator radiopaque marker relative to the one or more reference radiopaque markers can measure an axial length of the prosthetic valve indicative of a corresponding diameter of the prosthetic valve.

Certain embodiments of the disclosure concern further concern a method for implanting a prosthetic valve. The method can include positioning a prosthetic valve at a target site in a patient's body using a delivery apparatus, radially expanding the prosthetic valve from a radially compressed state to a radially expanded state, and monitoring a diameter of the prosthetic valve based on positional change of an indicator radiopaque marker relative to one or more reference radiopaque markers under fluoroscopy. The indicator and reference radiopaque markers can be located on the delivery apparatus.

Certain embodiments of the disclosure concerns a delivery apparatus configured to provide visual feedback of radial expansion of a prosthetic valve. The delivery apparatus can include an indicator arm changeable between a first configuration and a second configuration, the second configuration being different from the first configuration in location or shape of the indicator arm. The indicator arm can be configured to remain in the first configuration when a diameter of the prosthetic valve is smaller than a first predetermined size, and change to the second configuration when the diameter of the prosthetic valve is expanded to the first predetermined size.

Certain embodiments of the disclosure also concern a medical assembly that includes a prosthetic valve and a delivery apparatus configured to radially expand and compress the prosthetic valve. The delivery apparatus can include an indicator arm that is changeable between a first configuration and a second configuration. The indicator arm in the second configuration can have a different location or shape than in the first configuration. The indicator arm can be configured to remain in the first configuration when a diameter of the prosthetic valve is smaller than a first predetermined size, and change to the second configuration when the diameter of the prosthetic valve is expanded to the first predetermined size.

Certain embodiments of the disclosure also concerns a method of implanting a prosthetic valve. The method can include positioning a prosthetic valve at a target site in a patient's body using a delivery apparatus. The delivery apparatus can include an indicator arm which is retained in a first configuration. The method can further include radially expanding the prosthetic valve from a radially compressed state to a radially expanded state, and determining that a diameter of the prosthetic valve reaches a predetermined size when the indicator arm is changed to a second configuration. The indicator arm in the second configuration can have a different location or shape than in the first configuration.

Certain embodiments of the disclosure also concerns a delivery apparatus configured to provide visual feedback of radial expansion of a prosthetic valve. The delivery apparatus can include an indicator arm moveable between a biased position and an unbiased position. The indicator arm can be configured to remain in the biased position when a diameter of the prosthetic valve is smaller than a first predetermined size, and move to the unbiased position when the diameter of the prosthetic valve is expanded to the first predetermined size.

Certain embodiments of the disclosure further concerns a medical assembly including a prosthetic valve and a delivery apparatus. The delivery apparatus can include an actuation member and an indicator arm attached to the actuation member. The actuation member can be detachably attached to an expansion mechanism of the prosthetic valve. The expansion mechanism can be configured to radially expand and compress the prosthetic valve. The indicator arm can be changeable between a first configuration and a second configuration. The indicator arm in the second configuration can have a different location or shape than in the first configuration. The indicator arm can be configured to remain in the first configuration when a diameter of the prosthetic valve is smaller than a first predetermined size, and change to the second configuration when the diameter of the prosthetic valve is expanded to the first predetermined size.

Certain embodiments of the disclosure further concern a method of providing a visual feedback on radial expansion of a prosthetic valve. The method can include connecting an actuation member to an expansion mechanism of the prosthetic valve. The actuation member can include an indicator arm retained in a first configuration. The method can further include actuating the expansion mechanism with the actuation member to radially expand the prosthetic valve from a radially compressed state to a radially expanded state, and determining that a diameter of the prosthetic valve reaches a predetermined size when the indicator arm is changed to a second configuration. The indicator arm in the second configuration can have a different location or shape than in the first configuration.

The foregoing and other objects, features, and advantages of the disclosed technology will become more apparent from the following detailed description, which proceeds with reference to the accompanying figures.

DETAILED DESCRIPTION

Described herein are examples of prosthetic implant delivery assemblies and components thereof which can improve a physician's ability to monitor and/or control the size of a mechanically-expandable prosthetic implant, such as prosthetic valves (e.g., prosthetic heart valves or venous valves), stents, or grafts, as well as lock the size of the prosthetic implant, during the implantation procedure. Prosthetic heart valves disclosed herein can be implanted within any of the native valves of the heart (the aortic, mitral, tricuspid and pulmonary valves).

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site.

Figure 1:
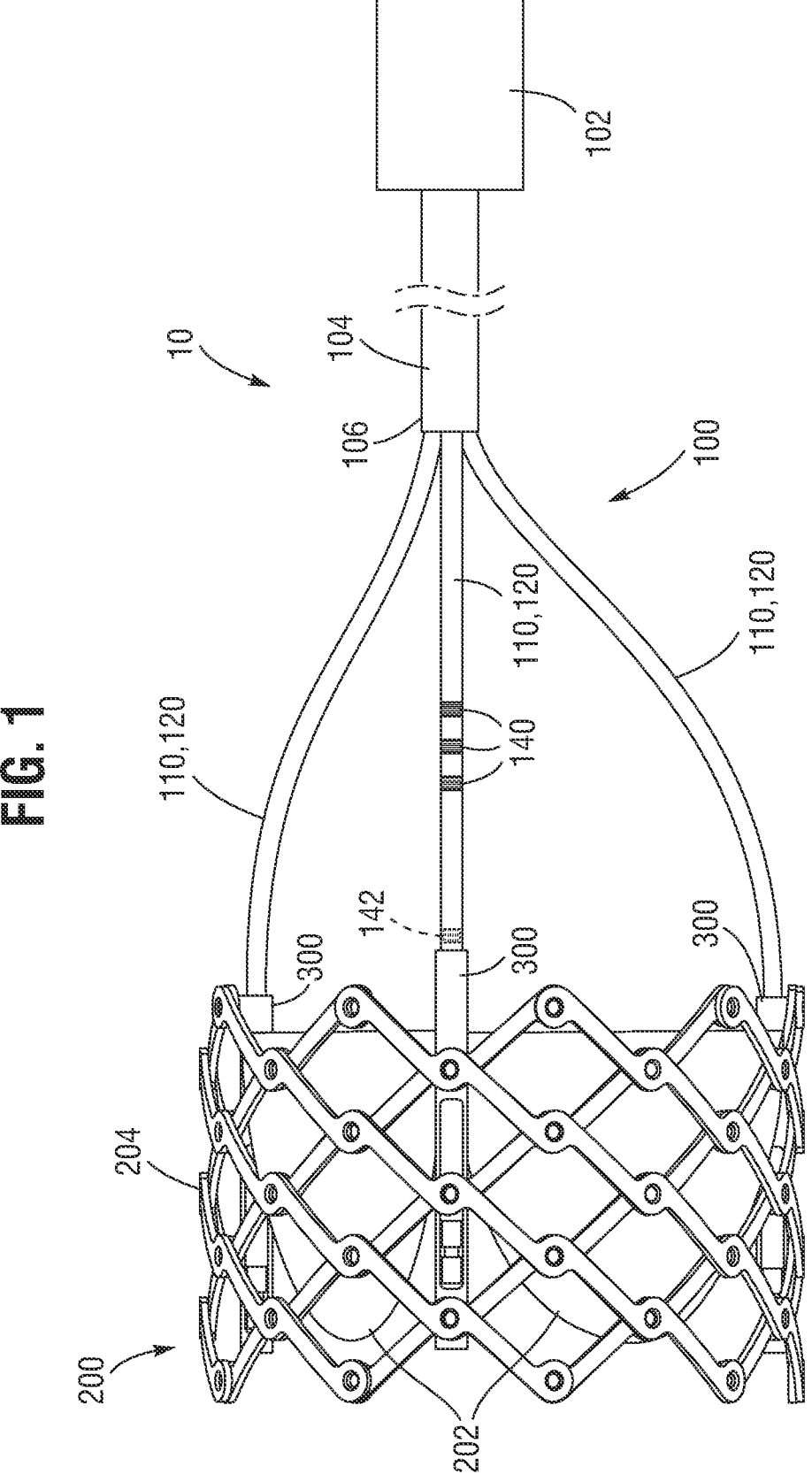
FIG. 1 is a side elevation view of an embodiment of a prosthetic valve delivery assembly.

FIG. 1 shows an example of a prosthetic implant delivery assembly 10 according to one embodiment of the present disclosure. The delivery assembly 10 can include two main components: a prosthetic valve 200 and a delivery apparatus 100. The prosthetic valve 200 can be releasably coupled to the delivery apparatus 100 via one or more retention and actuator assemblies 110, as further described below. It should be understood that the delivery apparatus 100 and other delivery apparatuses disclosed herein can be used to implant prosthetic devices other than prosthetic valves, such as stents or grafts.

The delivery apparatus 100 can include a handle 102 at a proximal end thereof. The delivery apparatus 100 can include one or more shafts 104 coupled to the handle 102. During delivery of the prosthetic valve 200, the handle 102 can be maneuvered by a surgeon to advance and retract the delivery apparatus 100 through the patient's vasculature. In some embodiments, the handle 102 can include a plurality of knobs or other actuating mechanisms for controlling different components of the delivery apparatus 100 in order to expand and/or deploy the prosthetic valve 10. For example, the handle 102 can include one or more knobs or other actuating mechanisms, each configured to manipulate a respective retention and actuator assembly 110 of the delivery apparatus 100 to interact with a corresponding valve expansion mechanism 300 (also referred to as "valve actuators") so as to expand or compress the prosthetic valve 200, and/or lock the prosthetic valve 200 in a desired diameter as described further below.

Figures 2A, 2B, 2C:
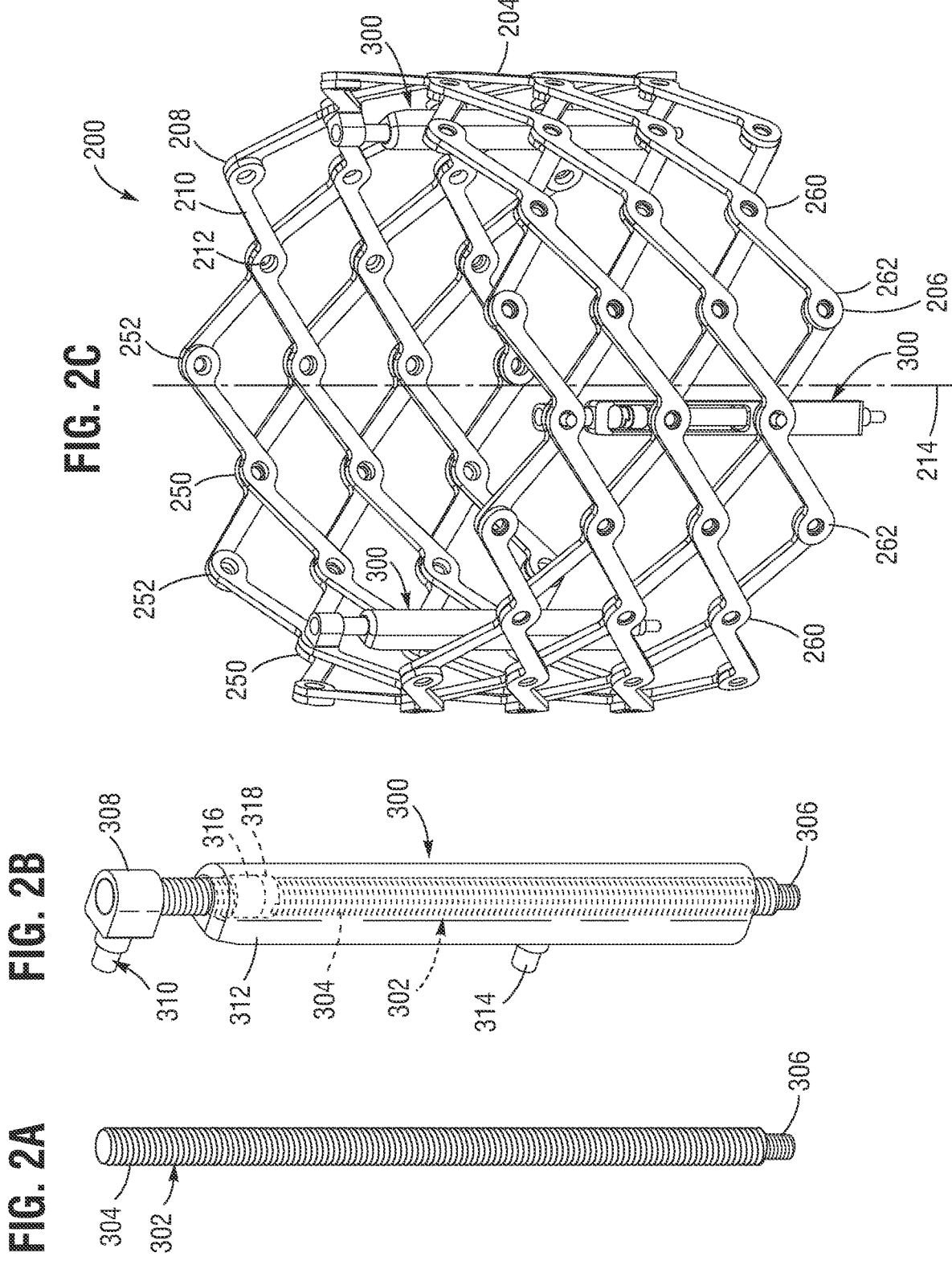
FIG. 2A is a side perspective view of an inner member of a valve expansion mechanism, according to one embodiment.
FIG. 2B is a side perspective view of a valve expansion mechanism.
FIG. 2C is a side perspective view of one embodiment of a prosthetic valve that includes multiple expansion mechanisms of the type shown in FIG. 2B.

FIG. 2C is a perspective view of the prosthetic valve 200. In particular embodiments, the prosthetic valve 200 can be implanted within the native aortic annulus, although it also can be implanted at other locations in the heart, including within the native mitral valve, the native pulmonary valve, and the native tricuspid valve. The prosthetic valve 200 can include an annular stent or frame 204 having a proximal end 206 and a distal end 208. In some embodiments, the proximal end 206 can be an outflow end and the distal end 208 can be an inflow end. In other embodiments, the proximal end 206 can be an inflow end and the distal end 208 can be the outflow end. For example, in a retrograde transfemoral approach of implanting a prosthetic valve, the proximal end 206 can be the outflow end and the distal end 208 can be the inflow end. In another example, in an antegrade transseptal route for implanting the prosthetic valve, the proximal end 206 can be the inflow end and the distal end 208 can be the outflow end.

The prosthetic valve 200 can also include a valvular structure 202 which is mounted to the frame 204 and configured to regulate the flow of blood through the prosthetic valve 200 from the inflow end to the outflow end. For example, the valvular structure can include a leaflet assembly comprising one or more leaflets made of a flexible material. The leaflets of the leaflet assembly can be made from in whole or part, biological material, bio-compatible synthetic materials, or other such materials. Suitable biological material can include, for example, bovine pericardium (or pericardium from other sources). Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, and 8,252,202, and U.S. Patent Application No. 62/614,299, all of which are incorporated herein by reference in their entireties.

Although not shown, the prosthetic valve 200 can also include one or more skirts or sealing members. For example, the prosthetic valve 200 can include an inner skirt mounted on the inner surface of the frame. The inner skirt can function as a sealing member to prevent or decrease perivalvular leakage, to anchor the leaflets to the frame, and/or to protect the leaflets against damage caused by contact with the frame during crimping and during working cycles of the prosthetic valve. The prosthetic valve 200 can also include an outer skirt mounted on the outer surface of the frame 204. The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., PET) or natural tissue (e.g., pericardial tissue).

The frame 204 can be made of any of various suitable materials, such as stainless steel, a cobalt-chrome alloy (e.g., MP35N alloy), or a nickel titanium alloy ("NiTi"), for example Nitinol. As shown, the frame 204 can include a plurality of interconnected struts 210 arranged in a lattice-type pattern. The struts 210 are shown as positioned diagonally, or offset at an angle relative to, and radially offset from, a longitudinal axis 214 of the prosthetic valve 200 when the prosthetic valve 200 is in the expanded configuration. In other implementations, the struts 210 can be offset by a different amount than depicted in FIG. 2C, or some or all of the struts 210 can be positioned parallel to the longitudinal axis of the prosthetic valve 200.

In the illustrated embodiment, the struts 210 are pivotably coupled to one another at one or more pivot joints along the length of each strut. For example, each of the struts 210 can be formed with apertures 212 at opposing ends of the strut and apertures 212 spaced along the length of the strut. Respective hinges can be formed at the locations where struts 210 overlap each other via fasteners, such as rivets or pins 216 (see e.g., FIG. 3) that extend through the apertures. The hinges can allow the struts 210 to pivot relative to one another as the frame 204 is radially expanded or compressed, such as during assembly, preparation, or implantation of the prosthetic valve 200.

In some embodiments, the frame 204 can be constructed by forming individual components (e.g., the struts and fasteners of the frame) and then mechanically assembling and connecting the individual components together. In other embodiments, the struts 210 are not coupled to each other with respective hinges but are otherwise pivotable or bendable relative to each other to permit radial expansion and contraction of the frame 204. For example, the frame 204 can be formed (e.g., via laser cutting, electroforming or physical vapor deposition) from a single piece of material (e.g., a metal tube). Further details regarding the construction of the frame and the prosthetic valve that can be used with the delivery apparatuses disclosed herein are described in U.S. Patent Applications Nos. 2018/0153689, 2018/0344456, 2015/0135506, 2014/0296962, and U.S. patent application Ser. No. 16/105,353, all of which are incorporated herein by reference.

As alluded to above, the prosthetic valve 200 can further include one or more valve expansion mechanisms 300. As shown in FIG. 1, each of the expansion mechanisms 300 can be configured to form a releasable connection with a respective retention and actuator assembly 110 of the delivery apparatus 100. In some embodiments, the valve expansion mechanisms 300 can be mounted to and equally spaced around an inner surface of the frame 204. For example, FIG. 2C shows three valve expansion mechanisms 300 equally spaced around the inner surface of the frame 204. It should be understood that the prosthetic valve 200 can have any number of valve expansion mechanisms, which could be mounted on outer surface of the frame or spaced unequally around the frame.

As described below, the valve expansion mechanisms 300 can be used to radially expand or compress the prosthetic valve 200. In some embodiments, the valve expansion mechanisms 300 can also be used to lock the prosthetic valve 200 in a radially expanded state.

Referring to FIGS. 2A-2C, the valve expansion mechanism 300 in the illustrated embodiment can include an inner member or actuator screw 302 (which functions as a linear actuator or a push-pull member in the illustrated embodiment) comprising a relatively long upper, or distal, portion 304 and a relatively shorter lower, or proximal, portion 306 at the proximal end of the actuator screw 302, wherein the proximal portion 306 has a smaller diameter than the upper portion 304. Both the distal and proximal portions 304, 306 of the actuator screw 302 can have externally threaded surfaces.

The actuator screw 302 can have a distal attachment piece 308 attached to its distal end having a radially extending distal valve connector 310. The distal attachment piece 308 can be fixed to the actuator screw 302 (e.g., welded together or manufactured as one piece). The distal valve connector 310 can extend through an opening at or near the distal end of the frame 204 formed at a location on the frame where two or more struts intersect as shown in FIG. 2C. The distal valve connector 310 can be fixed to the frame 204 (e.g., welded). Due to the shape of the struts, the distal end of the frame 204 comprises an alternating series of distal junctions 250 and distal apices 252. In the illustrated example, the distal valve connectors 310 of the three valve expansion mechanisms 300 are connected to the frame 204 through distal junctions 250. In other examples, one or more distal valve connectors 310 can be connected to the frame 204 through distal apices 252. In other embodiments, the distal valve connectors 310 can be connected to junctions closer to the proximal end 206 of the frame 204.

The valve expansion mechanism 300 can further include an outer member or sleeve 312. The sleeve 312 can be positioned annularly around the distal portion 304 of the actuator screw 302 and can contain axial openings at its proximal and distal ends through which the actuator screw 302 can extend. The axial openings and the lumen in the sleeve 312 can have a diameter larger than the diameter of the distal portion 304 of the actuator screw 302 such that the screw can move freely within the sleeve (the actuator screw 302 can be moved proximally and distally relative to the sleeve 312). Because the actuator screw 302 can move freely within the sleeve, it can be used to radially expand and/or contract the frame 204 as disclosed in further detail below.

The sleeve 312 can have a proximal valve connector 314 extending radially from its outer surface. The proximal valve connector 314 can be fixed to the sleeve 312 (e.g., welded). The proximal valve connector 314 can be axially spaced from the distal valve connector 310 such that the proximal valve connector can extend through an opening at or near the proximal end of the frame 204. The proximal end of the frame 204 comprises an alternating series of proximal junctions 260 and proximal apices 262. In the illustrated example, the proximal valve connectors 314 of the three valve expansion mechanisms 300 are connected to the frame 204 through proximal junctions 260. In other examples, one or more proximal valve connectors 314 can be connected to the frame 204 through proximal apices 262. In other embodiments, the proximal valve connectors 314 can be connected to junctions closer to the distal end of the frame 204.

It should be understood that the distal and proximal connectors 310, 314 need not be connected to opposite ends of the frame 204. The valve expansion mechanism 300 can be used to expand and compress the frame 204 as long as the distal and proximal connectors are connected to respective junctions on the frame that are axially spaced from each other.

A locking nut 316 can be positioned inside of the sleeve 312 and can have an internally threaded surface that can engage the externally threaded surface of the actuator screw 302. The locking nut 316 can have a notched portion 318 at its proximal end, the purpose of which is described below. The locking nut can be used to lock the frame 204 into a particularly radially expanded state, as discussed below.

Figure 3:
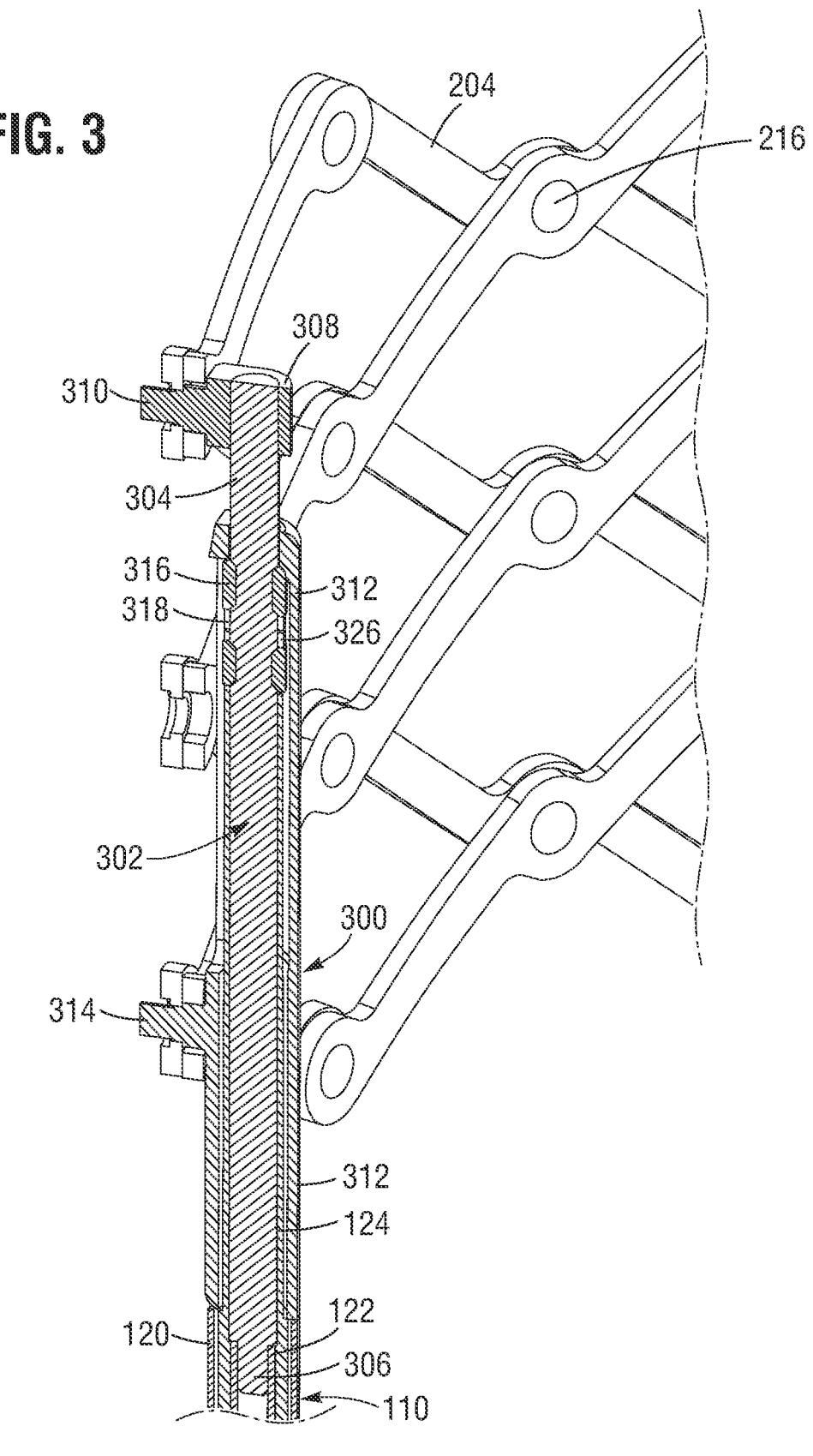
FIG. 3 is a cross-sectional view of one of the valve expansion mechanisms of FIG. 2B and components of a delivery apparatus.
Figure 4:
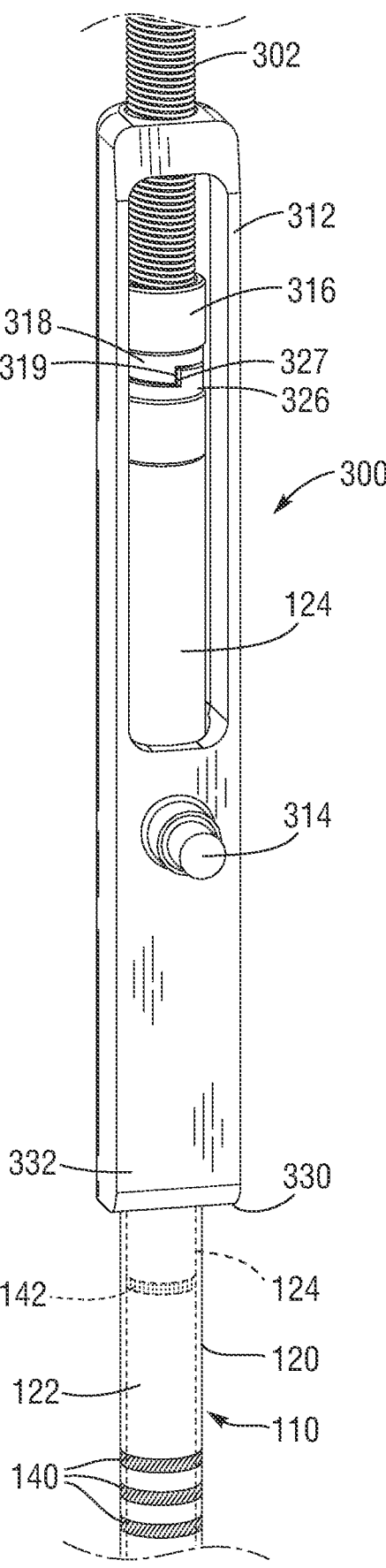
FIG. 4 is a perspective view of one of the valve expansion mechanisms of FIG. 2B and components of a delivery apparatus.

FIGS. 3-4 show one valve expansion mechanism 300 interfacing with components of a retention and actuator assembly 110 of the delivery apparatus 100. As shown, the retention and actuator assembly 110 includes a support tube 120, an actuator member 122, and a locking tool 124. The proximal end of the support tube 120 can be connected to a handle or other control device (not shown) that a doctor or operator of the delivery assembly utilizing to operate the valve expansion mechanism 300 as described herein. Similarly, the proximal ends of the actuator member 122 and the locking tool 124 can be connected to the handle.

The support tube 120 annularly surrounds a proximal portion of the locking tool 124 such that the locking tool 124 extends through a lumen of the support tube 120. The support tube 120 and the sleeve 312 are sized such that the distal end of the support tube 120 can abut or engage the proximal end 330 of the sleeve 312 such that the support tube 120 is prevented from moving distally beyond the sleeve 312.

The actuator member 122 can extend through a lumen of the locking tool 124. The actuator member 122 can be, for example, a shaft, a rod, a cable, or wire. The distal end portion of the actuator member 122 can be releasably connected to the proximal portion 306 of the actuator screw 302. For example, the distal end portion of the actuator screw 302 can have an internally threaded surface that can engage the external threads of the proximal portion 306 of the actuator screw 302. Alternatively, the actuator member can have external threads that engage an internally threaded portion of the screw. Other releasable connection mechanisms (e.g., hoop-and-loop, buckle, clip, magnetic, etc.) can also be used. Thus, when the actuator member 122 is threaded onto the actuator screw 302, axial movement of the actuator member 122 can cause axial movement of the actuator screw 302.

The distal portion of the locking tool 124 can annularly surround the actuator screw 302 and extend through a lumen of the sleeve 312 and the proximal portion of the locking tool 124 can annularly surround the actuator member 122 and extends through a lumen of the support tube 120 to the handle 102 of the delivery apparatus 100. The locking tool 124 can have an internally threaded surface that can engage the externally threaded surface of the actuator screw 302 such that clockwise or counter-clockwise rotation of the locking tool 124 causes the locking tool 124 to advance distally or proximally along the actuator screw 302, respectively.

The distal end of the locking tool 124 can comprise a notched portion 326, as can best be seen in FIG. 4. The notched portion 326 of the locking tool 124 can have an engagement surface 327 that is configured to engage a correspondingly shaped engagement surface 319 of the notched portion 318 of the locking nut 316 such that rotation of the locking tool (e.g., clockwise rotation) causes the locking nut 316 to rotate in the same direction (e.g., clockwise) and advance distally along the actuator screw 302. The notched portions 318, 326 in the illustrated embodiment are configured such that rotation of the locking tool 124 in the opposite direction (e.g., counter-clockwise) allows the notched portion 326 of the locking tool 124 to disengage the notched portion 318 of the locking nut 316; that is, rotation of the locking tool 124 in a direction that causes the locking tool 124 to move proximally does not cause corresponding rotation of the locking nut 316.

In alternative embodiments, the distal end portion of the locking tool 124 can have various other configurations adapted to engage the locking nut 316 and produce rotation of the locking nut upon rotation of the locking tool 124 for moving the nut distally, such as any of the tool configurations described herein. In some embodiments, the distal end portion of the locking tool 124 can be adapted to produce rotation of the locking nut 316 in both directions so as to move the locking nut 316 distally and proximally along the actuator screw 302.

In operation, prior to implantation, the actuator member 122 can be screwed onto the proximal portion 306 of the actuator screw 302 and the locking nut 316 can be rotated such that it is positioned at the proximal end of the actuator screw 302. The frame 204 can then be placed in a radially collapsed state and the delivery assembly 200 can be inserted into a patient. Once the prosthetic valve is at a desired implantation site, the frame 204 can be radially expanded as described herein.

To radially expand the frame 204, the support tube 120 can be held firmly against the sleeve 312. The actuator member 122 can then be pulled in a proximal direction through the support tube 120, such as by pulling on the proximal end of the actuator member 122 or actuating a control knob on the handle that produces proximal movement of the actuator member 122. Because the support tube 120 is being held against the sleeve 312, which is connected to a proximal end of the frame 204 by the proximal valve connector 314, the proximal end of the frame 204 is prevented from moving relative to the support tube 120. As such, movement of the actuator member 122 in a proximal direction can cause movement of the actuator screw 302 in a proximal direction (because the actuator member 122 is threaded onto the actuator screw 302), thereby causing the frame 204 to foreshorten axially and expand radially. Alternatively, the frame 204 can be expanded by moving the support tube 120 distally while holding the actuator member 122 stationary, or moving the support tube 120 distally while moving the actuator member 122 proximally.

After the frame 204 is expanded to a desired radially expanded size, the frame 204 can be locked at this radially expanded size as described herein. Locking the frame 204 can be achieved by rotating the locking tool 124 in one direction (e.g., clockwise) causing the notched portion 326 of the locking tool to engage the notched portion 318 of the locking nut 316, thereby advancing the locking nut 316 distally along the actuator screw 302. The locking tool 124 can be so rotated until the locking nut 316 abuts an internal shoulder at the distal end of the sleeve 312 and the locking nut 316 cannot advance distally any further (see e.g., FIG. 4). This will prevent the actuator screw 302 from advancing distally relative to the sleeve 312 and radially compressing the frame 204. However, in the illustrated embodiment, the locking nut 316 and the actuator screw 302 can still move proximally through the sleeve 312, thereby allowing additional expansion of the frame 204 either during implantation or later during a valve-in-valve procedure as described in U.S. Patent Publication 2018/0153689, which is incorporated herein by reference.

Once the frame 204 is locked in radially expanded state, the locking tool 124 can be rotated in a direction to move the locking tool 124 proximally (e.g., in a counter-clockwise direction) to decouple the notched portion 326 from the notched portion 318 of the locking nut 316 and to unscrew the locking tool 124 from the actuator screw 304. Additionally, the actuator member 122 can be rotated in a direction to unscrew the actuator member 122 from the proximal portion 306 of the actuator screw 302 (e.g., the actuator member 122 can be configured to disengage from the actuator screw 302 when rotated counter-clockwise). Once the locking tool 124 and the actuator member 122 are unscrewed from the actuator screw 304, they can be removed from the patient along with the support tube 120, leaving the actuator screw 302 and the sleeve 312 connected to the frame 204, as shown in FIG. 2C, with the frame 204 locked in a particular radially expanded state.

In an alternative embodiment, the locking tool 124 can be formed without internal threads that engage the external threads of the actuator screw 302, which can allow the locking tool 124 to be slid distally and proximally through the sleeve 312 and along the actuator screw 302 to engage and disengage the locking nut 316.

In yet another embodiment, instead of using the locking nut 316 and actuator screw 304 as described above, the frame can be locked at an expanded size using a different locking mechanism, such as a ratchet mechanism as described in U.S. Patent Publication No. 2018/0153689 and U.S. Patent Application No. 62/776,348, both of which are incorporated herein by reference.

Any of the delivery assemblies disclosed herein can have various handle configurations with one or more actuators or controls configured to produce movement of components of the assembly that expand and compress a prosthetic valve (or another type of implant). In some embodiments, the handle can have actuators that can be operated by a user by manually rotating and/or manually pushing/pulling actuators on the handle. In other embodiments, the actuators on the handle and/or other components of the assembly can be electrically, pneumatically and/or hydraulically controlled.

For example, in some embodiments, the handle 102 can house one or more electric motors that are actuated by a user to produce movement of components of the delivery assembly, such as one or more motors operable to produce linear movement of the actuator screws 302, and one or more motors operable to produce rotational movement of the locking tools 124 (for rotating locking nuts 316). In one specific implementation, one electric motor is used to produce linear movement of all of the actuators screws 302 mounted on the prosthetic valve and one electric motor is used to produce rotational movement of all of the locking tools 124 included in the assembly. In another implementation, one electric motor can be provided for each actuator screw and for each locking tool 124. Further details regarding handle configurations that include electric motors for controlling delivery assembly components are disclosed in U.S. Publication No. 2014/0296962, which is incorporated herein by reference.

Additionally, any of the delivery assemblies disclosed herein can include software and/or hardware operable to control expansion of a prosthetic valve, as further disclosed in U.S. Publication No. 2014/0296962. In particular embodiments, a delivery assembly can include a programmable controller (such as housed in the handle) that is operable to radially expand a prosthetic valve according to a specific algorithm. For example, a delivery assembly can include one or more motors (e.g., electric motors) that are controlled by an electronic controller to radially expand a prosthetic valve according to a specific algorithm. In certain implementations, for example, the controller can be programed to produce pulsatile radial expansion of a prosthetic valve, as further disclosed in U.S. Publication No. 2014/0296962.

As described below, the delivery apparatus 100 can be configured to provide real-time, visual feedback for radial expansion of the prosthetic valve 200. In certain embodiments, the delivery apparatus 100 can also be configured to provide visual confirmation that the prosthetic valve 200 is locked in a desired radially expanded size.

In one embodiment, one or more reference radiopaque markers 140 can be located on the outer surface of the support tube 120 in a retention and actuator assembly 110, and at least one indicator radiopaque marker 142 can be located on the outer surface of the locking tool 124 in the same retention and actuator assembly 110.

Each of the indicator and reference radiopaque markers 140, 142 can comprise radiopaque materials, such as gold, platinum, tungsten, platinum iridium alloy, palladium, etc., such that they are visible under fluoroscopy when the prosthetic valve is delivered into a patient's body by the delivery apparatus. The markers can be formed using any of various techniques known in the art. In some embodiments, the radiopaque markers 140 and 142 can be formed by means of radiopaque inks and adhesives, and applied on the delivery apparatus components in a number of ways, such as screen printing, high speed roller printing, coating, dipping, etc. In other embodiments, the markers can be separately formed components (e.g., in the form of annular rings or C-shaped bands that are mounted on the delivery apparatus components). Except for the reference radiopaque markers 140, a distal end portion of the support tube 120 can comprise a radiolucent material or have a cut-out window so that the indicator radiopaque marker 142 on the locking tool 124 is visible under fluoroscopy.

In some embodiments, the reference radiopaque markers 140 are configured to be visually distinguishable from the indicator radiopaque marker 142 under fluoroscopy. For example, the reference radiopaque markers 140 can have a different width and/or circumferential length than the indicator radiopaque marker 142.

As noted above, to radially expand the frame 204, the distal end of the support tube 120 can be held firmly against the sleeve 312 such that the proximal end of the frame 204 is prevented from moving relative to the support tube 120. Thus, the support tube 120 and the reference radiopaque markers 140 located thereof maintain a fixed spatial relationship relative to the proximal end 206 of the frame 204 during radial expansion of the prosthetic valve.

Also as noted above, pulling the actuator member 122 in the proximal direction through the support tube 120 can cause proximal movement of the actuator screw 302 (or the ratchet rack when the ratchet mechanism is used as described in U.S. Patent Publication No. 2018/0153689 or U.S. Patent Application No. 62/776,348), which in turn can cause the frame 204 to foreshorten axially and expand radially. Because the locking tool 124 is threadably coupled to the actuator screw 302, the locking tool 124 and the indicator radiopaque marker 142 located thereof maintain a fixed spatial relationship relative to the distal end 208 of the frame 204 during radial expansion of the prosthetic valve.

Thus, a position of the indicator radiopaque marker 142 relative to the one or more reference radiopaque markers 140 can measure an axial length (i.e., the distance between the proximal end 206 and distal end 208) of the frame 204 which is indicative of a corresponding diameter of the prosthetic valve as it is radially expanded from a radially compressed state to a radially expanded state. In other words, the reference radiopaque markers 140 can effectively function as a "scale" and the indicator radiopaque marker 142 can effectively function as a "dial" or "pointer" such that a location of the "dial" relative to the "scale" can indicate a corresponding diameter of the prosthetic valve.

Accordingly, as an operator radially expands the prosthetic valve by actuating the valve expansion mechanism 300, the operator can monitor and/or measure in real-time the diameter of the prosthetic valve based on the alignment of the indicator radiopaque marker 142 with any one of the reference radiopaque markers 140 under fluoroscopy.

The indicator radiopaque marker 142 desirably is configured to be positioned outside of the frame 204 to ensure that the indicator radiopaque marker 142 is always visible under fluoroscopy during radial expansion of the prosthetic valve. For example, in some embodiments, the indicator radiopaque marker 142 can be located along the proximal portion of the locking tool 124 between the proximal end 206 of the frame 204 and the proximal end 330 of the sleeve 312. In other embodiments, the indicator radiopaque marker 142 can be located along the proximal portion of the locking tool 124 proximal to the proximal end 330 of the sleeve 312.

Figure 5:
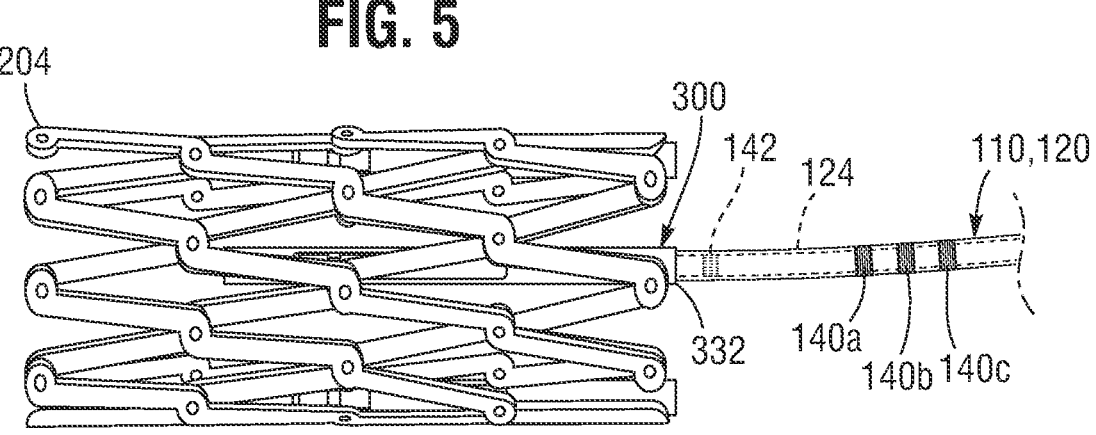
FIG. 5 shows a prosthetic valve in a radially compressed configuration.
Figure 6:
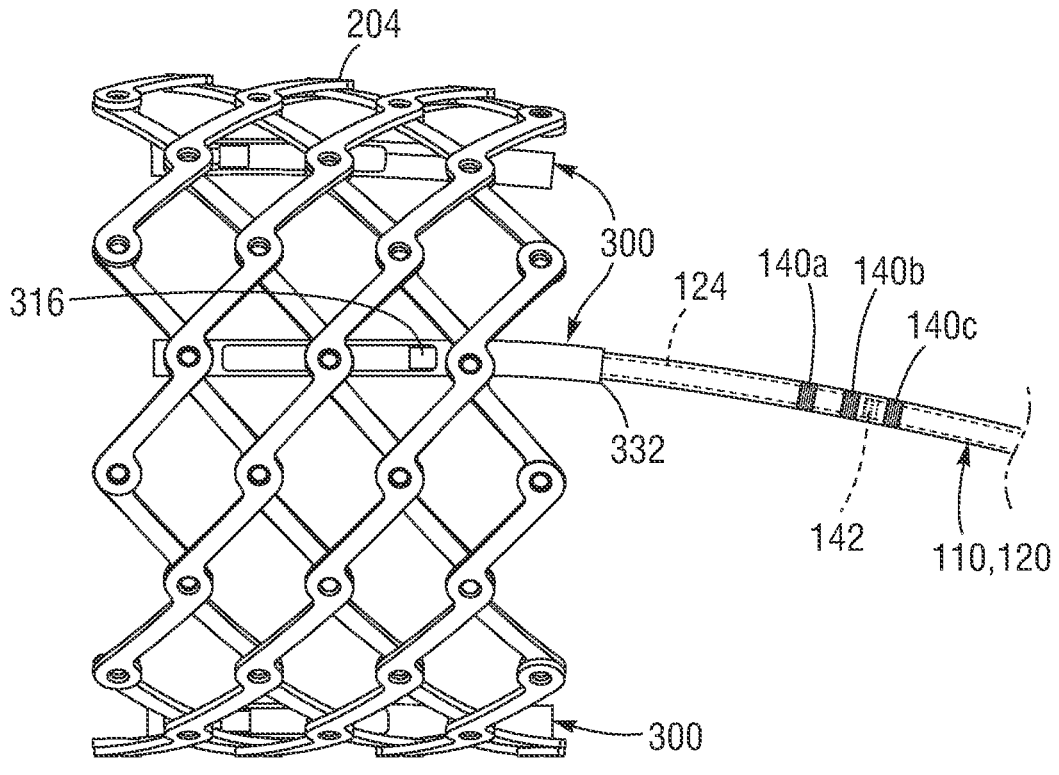
FIG. 6 shows the prosthetic valve of FIG. 5 in a radially expanded configuration with an unlocked radial diameter.
Figure 7:
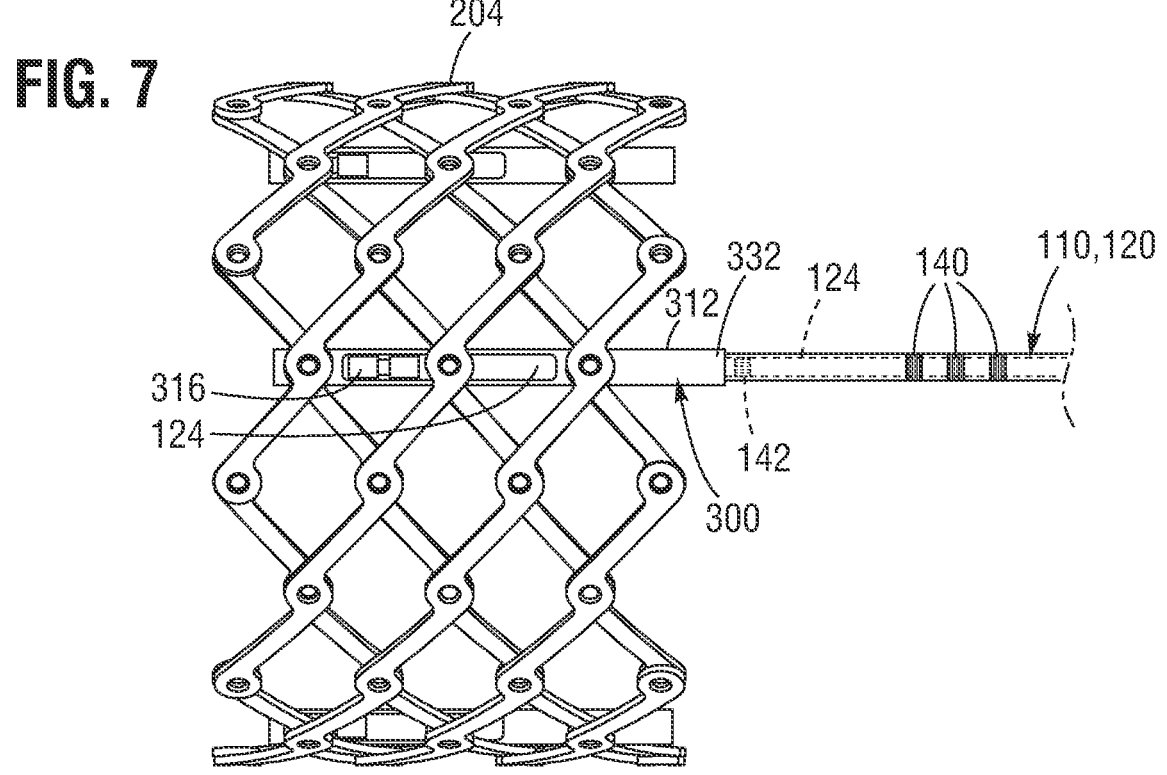
FIG. 7 shows the prosthetic valve of FIG. 5 after a locking mechanism is actuated to lock the prosthetic valve in the expanded state.

As noted above, the support tube 120 can include a plurality of reference radiopaque markers 140. For example, FIGS. 5-7 show three reference radiopaque markers 140a, 140b, 140c, although it should be understood any number of reference radiopaque markers 140 can be used. Each reference radiopaque marker 140 can correspond to a specific diameter of the prosthetic valve. For example, while the prosthetic valve is expanded from the radially compressed state to the radially expanded state, alignment of the indicator radiopaque marker 142 with the distal-most reference radiopaque marker 140a can indicate a first expanded diameter of the prosthetic valve, alignment of the indicator radiopaque marker 142 with the intermediate reference radiopaque marker 140b can indicate a second expanded diameter of the prosthetic valve, wherein the second diameter is greater than the first diameter, and alignment of the indicator radiopaque marker 142 with the proximal-most reference radiopaque marker 140c can indicate a third expanded diameter of the prosthetic valve, wherein the third diameter is greater than the second diameter.

In the depicted examples, a more distally located reference radiopaque marker indicates a smaller diameter of the prosthetic valve than a more proximally located reference radiopaque marker. For example, the prosthetic valve can be expanded to a diameter within a working range defined by a smallest diameter Dmin and a largest diameter Dmax. Thus, reference radiopaque marker 140a can indicate the smallest diameter Dmin, and reference radiopaque marker 140c can indicate the largest diameter Dmax, and reference radiopaque marker 140b can indicate an intermediate diameter Dmed. In an exemplary embodiment, reference radiopaque markers 140a, 140b, and 140c can indicate the prosthetic valve being expanded to the diameter of 27 mm, 28 mm, and 29 mm, respectively.

It should be understood that the support tube 120 can have any number of reference radiopaque markers. For example, the number of reference radiopaque markers 140 can be only 1 or 2, or more than 3.

In some embodiments, the multiple reference radiopaque markers 140 located on the support tube 120 are spaced evenly with equal distance between any two adjacent reference radiopaque markers. In other embodiments, the multiple reference radiopaque markers 140 can be spaced with unequal distances.

While the embodiments depicted in FIGS. 5-7 show only one expansion mechanism 300 being coupled to a retention and actuator assembly 110, it should be understood that each of the expansion mechanisms can be connected to a corresponding retention and actuator assembly, as illustrated in FIG. 1. In some embodiments, only one of, or selected ones of the retention and actuator assemblies 110 can have a corresponding set of an indicator and reference radiopaque markers. In other embodiments, each of the retention and actuator assemblies can contain respective indicator and reference radiopaque markers so as to facilitate an operator to view the radiopaque markers irrespective of the angular position of the prosthetic valve.

While the embodiments depicted in FIGS. 5-7 show only one type of expansion and locking mechanism 300 being coupled to a retention and actuator assembly 110, it should be understood that the same concept of using radiopaque markers to indicate the radial diameter of the prosthetic valve and/or locking confirmation of the frame may be applied when other expansion and locking mechanisms are used, such as ratchet mechanism as described in U.S. Patent Publication No. 2018/0153689 or U.S. Patent Application No. 62/776,348.

As described above and further illustrated in FIGS. 6-7, the frame 204 can be locked at the radially expanded size by rotating the locking tool 124 to advance the locking nut 316 to the distal end of the sleeve 312. According to one embodiment, at least one radiopaque marker can be used to visually confirm under fluoroscopy that the locking nut 316 is moved to the desired location for locking the frame 204.

For example, the indicator radiopaque marker 142 can be configured to align with or come into close proximity with the proximal end portion 332 of the sleeve 312 when the locking tool 124 advances the locking nut 316 to the distal end of the sleeve 312. In one embodiment, the proximal end portion 332 of the sleeve 312 can comprise a radiopaque marker so that it is visible under fluoroscopy. In other embodiments, the proximal end portion 332 of the sleeve 312 does not contain a radiopaque marker. Instead, the proximal end portion 332 of the sleeve 312 can be sized and/or shaped to be visually distinguishable from the surrounding structures under fluoroscopy. For example, the proximal end portion 332 can have a larger diameter than the distal end support tube 120. Thus, locking of the frame 204 can be confirmed by verifying that the indicator radiopaque marker 142 is aligned with the proximal end portion 332 of the sleeve 312. As examples, FIG. 6 shows the indicator radiopaque marker 142 in "unlocked" position spaced proximally from frame 204, whereas FIG. 7 shows the indicator radiopaque marker 142 in "locked" position that aligns with or in close proximity to the proximal end portion 332 of the sleeve 312.

In some embodiments, the delivery apparatus 100 includes only one set of radiopaque markers (e.g., markers 140 and 142) that are used to provide both visual feedback on radial diameter of the prosthetic valve and visual confirmation of the locking of the frame. In other embodiments, the delivery apparatus can include one set of radiopaque markers that are used for visual feedback of the radial diameter of the prosthetic valve only, and/or one or more different radiopaque markers that are used for visual confirmation of the locking of the frame.

Alternative Embodiments for Monitoring Valve Expansion and Confirming Frame Locking Although the systems and methods for monitoring valve expansion and confirming frame locking have been described in conjunction with specific embodiments as illustrated in FIGS. 1-7, it should be appreciated that the disclosed embodiments are non-limiting examples and the general concept disclosed herein can be implemented in alternative embodiments.

For example, in certain embodiments, the indicator radiopaque marker can be located on the actuator member 122 instead of the locking tool 124. Since valve expansion is caused by pulling the actuator member 122 in the proximal direction relative to the support tube 120, position of the indicator radiopaque marker on the actuator member 122 relative to the reference radiopaque markers on the support tube 120 can also indicate the diameter of the prosthetic valve during radial expansion.

In other embodiments, the relative locations of the indicator radiopaque marker and reference radiopaque markers can be switched. For example, one or more reference radiopaque markers can be located on the outer surface of the locking tool 124, and at least one indicator radiopaque marker can be located on the outer surface of the support tube 120. Thus, the indicator radiopaque marker remains stationary while the reference radiopaque markers move axially relative to indicator radiopaque marker during valve expansion. Similarly, alignment of the indicator radiopaque marker with the one or more of the reference radiopaque markers can indicate a corresponding expanded diameter of the prosthetic valve.

While the valve expansion mechanism 300 described above comprises a moving inner member (actuator screw 302) and a fixed outer member (sleeve 312), it should be appreciated that the valve expansion mechanism can be configured differently so long as it allows pushing the first end toward the second end of the prosthetic valve, or vice versa. In some embodiments, the first end is the inflow end and the second end is the outflow end. In other embodiments, the first end is the outflow end and the second end is the inflow end.

For example, in the embodiments described above with respect to FIGS. 5-6, the prosthetic valve can be expanded by holding a proximal end of the prosthetic valve stationary while pulling the inner member in the proximally direction relative to the outer member. In other embodiments, the prosthetic valve can be expanded by holding a distal end of the prosthetic valve stationary while pushing the inner member in the distal direction relative to the outer member. In still other embodiments, the prosthetic valve can be expanded by pushing the proximal end in the distal direction while pulling the distal end in the proximal direction.

Alternatively, the valve expansion mechanism can be configured to have a fixed inner member and a moveable outer member that annularly surrounds the inner member. To expand the prosthetic valve, the outer member can be configured to hold the inflow end (or outflow end) of the prosthetic valve stationary and the inner member can be configured to pull (or push) the outflow end (or inflow end) toward the inflow end (or outflow end) of the prosthetic valve.

More generally, the valve expansion mechanism can be configured to have two members that can be moved axially relative to each other. In some embodiments, the two members can be arranged side-by-side instead of coaxially. To expand the prosthetic valve, one member can be configured to hold the inflow end (or outflow end) of the prosthetic valve stationary and the other member can be configured to pull (or push) the outflow end (or inflow end) toward the inflow end (or outflow end) of the prosthetic valve.

Irrespective of how the valve expansion mechanism is configured, monitoring the diameter of an expanded prosthetic valve can be achieved by applying the same concept described above. For example, the delivery apparatus can comprise a first portion releasably connected to a first member of the valve expansion mechanism, a second portion releasably connected to a second member of the valve expansion mechanism, and the first and second members are configured to be axially moveable relative to each other. One or more reference radiopaque markers can be located on the first portion (or second portion), and an indicator radiopaque marker can be located on the second portion (or first portion). Axial movement of the second portion relative to the first portion can cause corresponding axial movement between the first and second members, thereby causing axial compression and radial expansion of the prosthetic valve. As such, alignment of the indicator radiopaque marker with the one or more reference radiopaque markers can indicate the diameter of the expanded prosthetic valve.

Although the prosthetic valve has been described to have a mechanically expandable frame, it should be appreciated that the same concept disclosed herein can also be applied to other types of prosthetic valves, such as balloon expandable prosthetic valves and self-expandable prosthetic valves. For example, the delivery apparatus can comprise a first portion releasably connected to an inflow end (or outflow end) of the prosthetic valve, and a second portion releasably connected to an outflow end (or inflow end) of the prosthetic valve. One or more reference radiopaque markers can be located on the first portion (or second portion), and an indicator radiopaque marker can be located on the second portion (or first portion). As the prosthetic valve is radially expanded, either through a self-expanding mechanism or by inflating an inflatable balloon, the distance between the inflow and outflow ends of the prosthetic valve is shortened. As a result, the second portion moves axially relative to the first portion. Thus, alignment of the indicator radiopaque marker with the one or more reference radiopaque markers can indicate the diameter of the expanded prosthetic valve.

Figure 8:
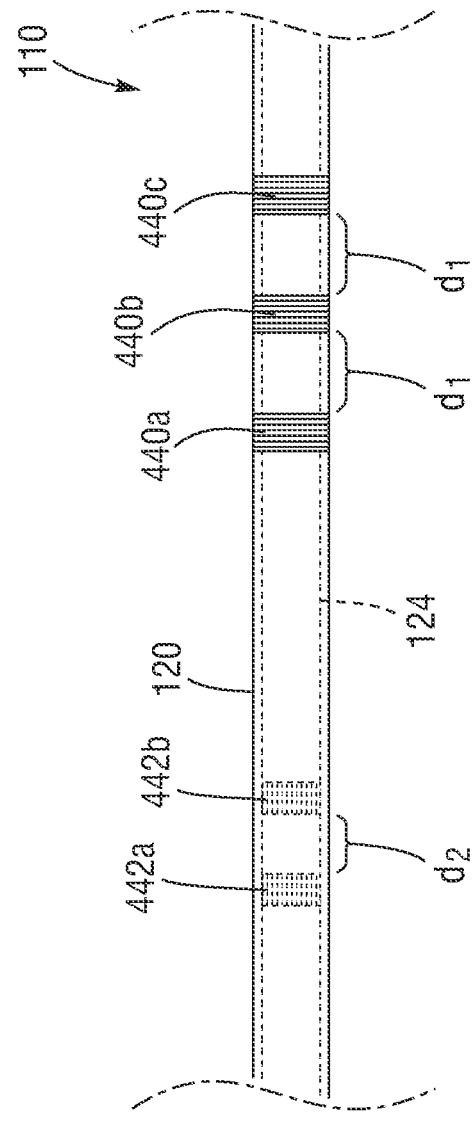
FIG. 8 illustrates an alternative embodiment of a portion of a delivery apparatus having multiple indicator radiopaque markers and multiple reference radiopaque markers.

In yet another embodiment, more than one indicator radiopaque markers can be used in conjunction with one or more reference radiopaque markers. For example, FIG. 8 illustrates an embodiment of a retention and actuator assembly 110 having three reference radiopaque markers 440a, 440b, 440c equally spaced by distance d1 and two indicator radiopaque markers 442a, 442b spaced by a distance d2, which can, for example, one-half of d1. The diameter of the prosthetic valve is indicated as D1, D2, or D3 when the proximal-most indicator radiopaque marker 442b is respectively aligned with the reference radiopaque marker 440a, 440b, or 440c. On the other hand, when the proximal-most indicator radiopaque marker 442b is located between reference radiopaque markers 440a and 440b (or between 440b and 440c) and the distal-most indicator radiopaque marker 442a is aligned with the reference radiopaque marker 440a (or 440b), then the diameter of the prosthetic valve can be indicated as an intermediate value between D1 and D2 (or between D2 and D3), e.g., the average of D1 and D2 (or the average of D2 and D3). Thus, using multiple indicator radiopaque markers with different spacing than reference radiopaque markers can provide different resolutions of measurement of the valve's diameter.

It should be understood that the retention and actuator assembly can be configured to have any number of indicator radiopaque markers and any number of reference radiopaque markers. The inter-marker spacing between indicator radiopaque markers can be larger or smaller than the inter-marker spacing between reference radiopaque markers. Further, the inter-marker spacing between indicator radiopaque markers and/or the inter-marker spacing between reference radiopaque markers can be uniform or non-uniform.

Embodiments of Using an Indicator Arm for Monitoring Valve Expansion

Some embodiments of the disclosure also concern using an indicator arm for monitoring radial expansion of a prosthetic valve, as described below. The indicator arms described below can be implemented in a delivery apparatus, such as delivery apparatus 100, with or without the radiopaque markers described above.

Figures 9A, 9B, 10:
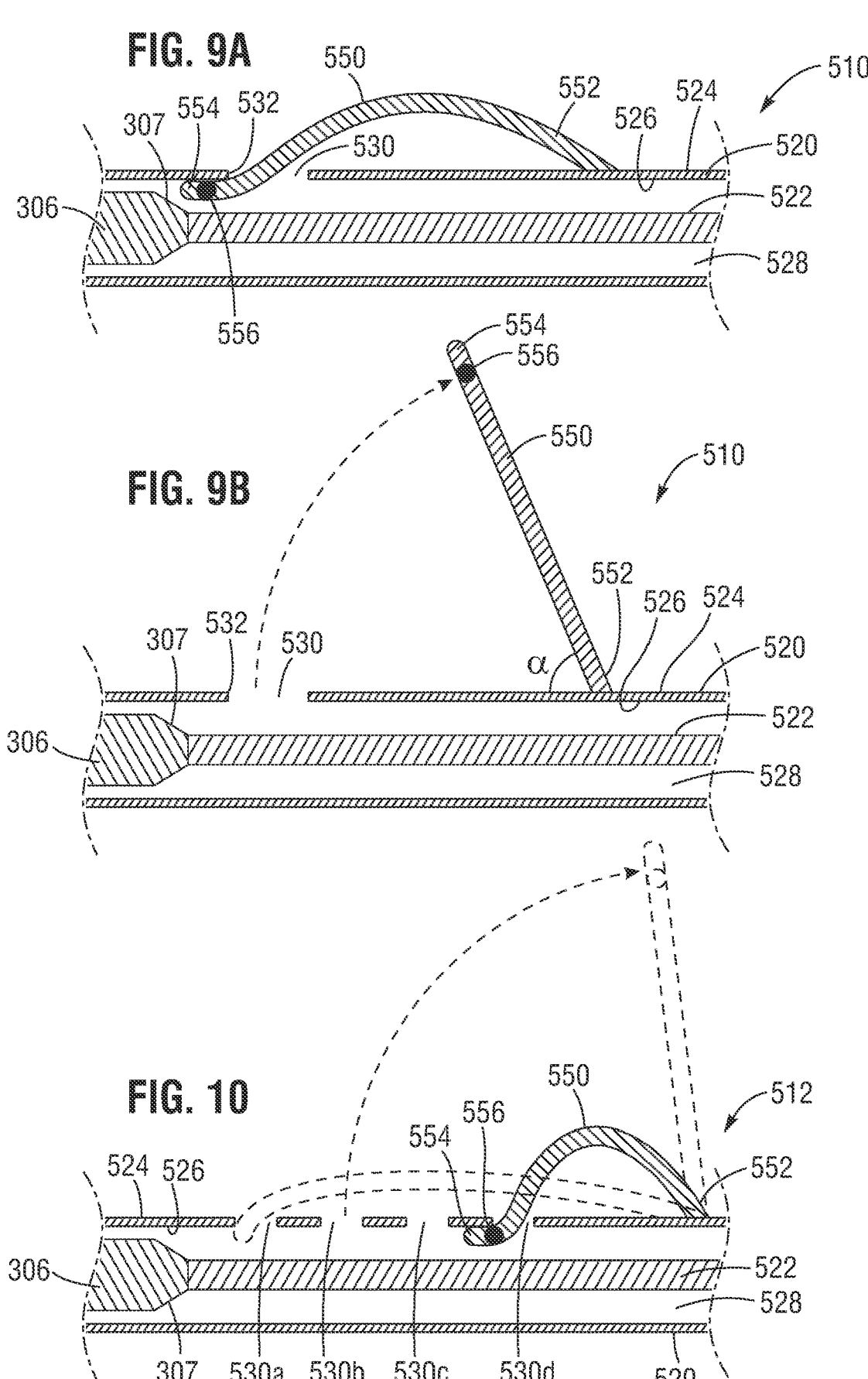
FIG. 9A illustrates a portion of a delivery apparatus having an indicator arm retained in a first configuration, according to a first embodiment.
FIG. 9B illustrates the portion of the delivery apparatus of FIG. 9A, wherein the indicator arm is changed to a second configuration.
FIG. 10 illustrates a portion of a delivery apparatus having an indicator arm according to a second embodiment.

FIGS. 9A-9B show a distal portion of a retention and actuator assembly 510 of a delivery apparatus, according to one embodiment. The retention and actuator assembly 510 includes a support tube 520 (also referred to as the "first actuation component") and an actuator member 522 (also referred to as the "second actuation component"). The support tube 520 has an outer surface 524 and an inner surface 526. The inner surface 526 defines a lumen 528 through which the actuator member 522 extends. The actuator member 522 can move axially within the lumen 528 relative the support tube 520.

Similar to the retention and actuator assembly 110, the retention and actuator assembly 510 can be configured to interface with a valve expansion mechanism 300 of a prosthetic valve 200, as shown in FIGS. 1-7 and described above. For example, the distal end of the support tube 520 can abut or engage the proximal end of the sleeve 312 of the valve expansion mechanism 300, and the distal end portion of the actuator member 522 can be releasably connected to the proximal portion 306 of the actuator screw 302 of the valve expansion mechanism 300.

For simplicity, FIGS. 9A-9B, as well as FIGS. 10-12 described below, only show the proximal portion 306 of the actuation screw 302, whereas other detailed structure of the valve expansion mechanism 300 and the prosthetic valve 200 are omitted.

Similar to operating the retention and actuator assembly 110, axially moving the actuator member 522 relative to the support tube 520 can actuate the valve expansion mechanism and cause radial expansion or compression of the prosthetic valve. For example, the prosthetic valve can be expanded by holding stationary the support tube 520 (which can abut the sleeve 312) while pulling the actuator member 522 (which can be connected to the actuator screw 302) in a proximal direction. Alternatively, the prosthetic valve can be expanded by pushing the support tube 520 distally while holding the actuator member 522 stationary, or pushing the support tube 520 distally while pulling the actuator member 522 proximally.

The support tube 520 can have an indicator arm 550 that is changeable or moveable between a first configuration (see e.g., FIG. 9A) and a second configuration (see e.g., FIG. 9B). As described more fully below, the indicator arm 550 can be configured to remain in the first configuration when a diameter of the prosthetic valve is smaller than a predetermined size, and change to the second configuration when the diameter of the prosthetic valve is expanded to the predetermined size.

In some embodiments, the indicator arm 550 can include an elastic material such that the indicator arm 550 in the first configuration is in a biased state and the indicator arm 550 in the second configuration is in an unbiased state. When released from the first configuration, the indicator arm can self-expand or move to the second configuration under the natural resiliency of the elastic material. Thus, the first configuration can also be termed "biased position" and the second configuration can also be termed "unbiased position." The elastic material can be metal, alloy, plastic, or any other suitable materials, as known in the art. In particular embodiments, the indicator arm 550 can be made from Nitinol.

In the biased position, the indicator arm 550 can be oriented generally along an axial axis of the support tube 520 and the prosthetic valve connected thereof (not shown). In the unbiased position, the indicator arm 550 can be oriented in an oblique angle (a) relative to the axial axis of the support tube 520 (and the prosthetic valve connected thereof).

In some embodiments, the angle α can be between about 10 degrees to about 170 degrees. In some embodiments, the angle α can be between about 30 degrees to about 150 degrees. In some embodiments, the angle α can be between about 60 degrees to about 120 degrees. In some embodiments, the angle α can be between about 45 degrees to about 90 degrees. In some embodiments, the angle α can be about 90 degrees.

In some embodiments, the indicator arm 550 can be slightly arched or curved in the biased position (see e.g., FIG. 9A). In some embodiments, the indicator arm 550 can be substantially straight in the unbiased position (see e.g., FIG. 9B). In some embodiments, the indicator arm 550 can be substantially straight in both the biased and unbiased positions.

In the depicted embodiment, the indicator arm 550 has a first end 552 and a second end 554. The first end 552 can be fixedly attached to an outer surface 524 of the support tube 520, e.g., by means of thermal bonding, gluing, welding, mechanical fasteners, or any other suitable techniques. Alternatively, the indicator arm 550 can be integrally formed in the support tube 520 (e.g., laser cutting the support tube to form the indicator arm and then shape setting the indicator arm to be biased to the second configuration shown in FIG. 9B). The second end 554 of the indicator arm 550 is configured to be removably attached to the support tube 520.

For example, when the indicator arm 550 is in the biased position (see e.g., FIG. 9A), the second end 554 can be removably attached to the support tube 520 such that an imaginary line extending through the first and second ends 552, 554 is generally parallel to the axial axis of the support tube 520.

As shown in FIG. 9A, the support tube 520 can have an aperture 530 which is located distal to the first end 552 of the indicator arm 550 and proximal to the prosthetic valve (not shown). When the indicator arm 550 is in the biased position, the second end 554 of the indicator arm 550 can extend into the lumen 528 through the aperture 530. Further, the second end 554 can frictionally engage an edge 532 of the aperture 530 and/or an inner surface 526 of the support tube 520 adjacent the aperture 530 so as to retain the indicator arm 550 in the biased position.

In some embodiments, when radially expanding the prosthetic valve, a portion of the prosthetic valve can engage and push the second end 554 of the indicator arm 550 proximally so as to assist in releasing the second end 554 from the support tube 520, thereby allowing the indicator arm 550 to return to its unbiased position (see e.g., FIG. 9B).

For example, the proximal portion 306 of the actuation screw can have a larger diameter than the actuator member 522. Thus, when the distal end of the actuator member 522 is connected to the proximal end of the proximal portion 306, at least a peripheral portion 307 of the proximal end of the proximal portion 306 can extend radially outwardly of the actuation screw 522. In the depicted embodiment, the proximal end of the proximal portion 306 has a truncated cone shape. Thus, the peripheral portion 307 has a sloped surface relative to the actuator member 522. In other embodiments, the proximal end of the proximal portion 306 can have a cylindrical shape. Thus, the uncovered peripheral portion 307 can be perpendicular to the actuator member 522.

As noted above, moving the actuator member 522 in a proximal direction relative to the support tube 520 can cause the actuator screw to move proximally relative to the sleeve, thereby radially expanding the prosthetic valve. In some embodiments, when the actuator screw moves in the proximal direction, the peripheral portion 307 of the actuator screw can contact the second end 554 of the indicator arm 550 which is in the biased position. Further moving the actuator screw proximally can exert a force against the second end 554 sufficient to push the second end 554 proximally away from the edge 532 of the aperture 530 and/or the inner surface 526 of the support tube 520. As a result, the second end 554 can move out of the lumen 528 through the aperture 530 (i.e., released from the aperture 530) and the indicator arm 550 can return to its unbiased position as shown in FIG. 9B.

In some embodiments, the indicator arm 550 can have a radiopaque marker 556 such that the change of the indicator arm 550 from the biased position to the unbiased position can be visible under fluoroscopy, e.g., by observing the change of location of the radiopaque marker 556. In some embodiments, the radiopaque marker 556 can be located adjacent the second end 554. In some embodiments, the radiopaque marker 556 can be located in the middle portion of the indicator arm 550. In alternative embodiments, the entire arm 550 can be formed from a radiopaque material that is visible under fluoroscopy.

In the depicted embodiment, the aperture 530 can be so positioned on the support tube 520 that when the peripheral portion 307 of the actuator screw engages the second end 554 of the indicator arm 550 and releases the second end 554 from the aperture 530, the diameter of the prosthetic valve is expanded to the predetermined size. Thus, one can determine that the prosthetic valve has been expanded to the predetermined size when observing (e.g., under fluoroscopy) the indicator arm 550 changes from the biased position to the unbiased position.

Although not shown, it should be understood that a different part of the prosthetic valve other than the peripheral portion 307 of the actuator screw, or even a portion of the retention and actuator assembly 510 itself, can be configured to engage the second end 554 of the indicator arm 550 and release it from the aperture 530. For example, the distal end portion of the actuator member 522 can have a shoulder portion (not shown) protruding radially outwardly of the actuator member 522, and such shoulder portion can be configured to contact the second end 554 and push it out of the lumen 528 through the aperture 530 when moving the actuator member 522 in the proximal direction. The same principle described herein applies as long as the second end 554 of the indicator arm 550 can be released from the aperture 530 by any part of the prosthetic valve or the delivery apparatus when the prosthetic valve is expanded to the predetermined size.

FIG. 10 shows another embodiment of a retention and actuator assembly 512 that is similar to the retention and actuator assembly 510 described above, except that the support tube 520 can have a plurality of apertures 530a, 530b, 530c, 530d (four in the illustrated example) that are located distal to the first end 552 of the indicator arm 550 and proximal to the prosthetic valve (not shown). Although four apertures are shown in FIG. 10, it should be understood that the number of apertures can be 2, 3, 5, or more.

The indicator arm 550 can be retained in the biased position when the second end 554 of the indicator arm 550 extends into the lumen 528 through any of the apertures 530a, 530b, 530c, 530d and frictionally engages the edge of the corresponding aperture or an inner surface 526 of the support tube 520 adjacent the corresponding aperture.

Similarly, when the actuator screw moves in the proximal direction (e.g., by moving the actuator member 522 in a proximal direction relative to the support tube 520), the peripheral portion 307 of the actuator screw can contact the second end 554 of the indicator arm 550 retained in the biased position, regardless which aperture (530a, 530b, 530c or 530d) the second end 554 extends through. Further moving the actuator screw proximally can push the second end 554 out of the lumen 528 through the corresponding aperture (530a, 530b, 530c or 530d) so as to allow the indicator arm 550 to return to its unbiased position.

In some embodiments, the apertures 530a, 530b, 530c, 530d can be spaced apart from each other such that each aperture corresponds to a different predetermined expanded diameter of the prosthetic valve. Prior to inserting the prosthetic valve into the patient's body, the user can insert the second end of the indicator arm 550 into an aperture corresponding to the desired expanded diameter for that particular patient. Thus, when the second end 554 of the indicator arm 550 is released from that aperture upon expansion of the prosthetic valve, the indicator arm 550 can move to its unbiased state, providing visual indication that the prosthetic valve has been expanded to the selected diameter.

For example, the four apertures 530a, 530b, 530c and 530d can correspond to four predetermined diameters of the prosthetic valve Da, db, Dc, and Dd, respectively. In some embodiments, the closer an aperture is to the first end 552 of the indicator arm 550, the larger is the corresponding predetermined diameter. For example, in the example depicted in FIG. 10, the predetermined diameters corresponding to the apertures 530a, 530b, 530c, 530d can be progressively larger, i.e., Da<db<Dc<Dd.

In an alternative embodiment, the retention and actuator assembly 512 can have multiple indicator arms (not shown), each of which is similar to the indicator arm 550 described above. Each of the indicator arms can have a first end fixedly connected to the support tube 520, and a second end that is removably attached to the support tube 520. For example, the retention and actuator assembly 512 can have four indicator arms. The first ends of the four indicator arms can be fixedly coupled to a proximal portion of the support tube 520 (the first ends can be fixed to the same location or spaced apart from each other on the proximal portion of the support tube 520). The second ends of the four indicator arms can respectively extend into the lumen 528 through the four apertures 530a, 530b, 530c and 530d so as to retain the four indicator arms in respective biased positions. Thus, continuously moving the actuator screw in the proximal direction can sequentially push the four second ends out of the lumen 528 through corresponding apertures (530a, 530b, 530c or 530d) so as to allow the corresponding indicator arms to return to their respective unbiased positions. As such, the four apertures can function as a scale such that an operator can monitor what diameter the prosthetic valve has been expanded to by observing which of the indicator arms has changed from its biased position to unbiased position. In some embodiments, the retention and actuator assembly 512 can have any number (e.g., 2, 3, 5, or more) of indicator arms with corresponding number of apertures.

Figure 11:
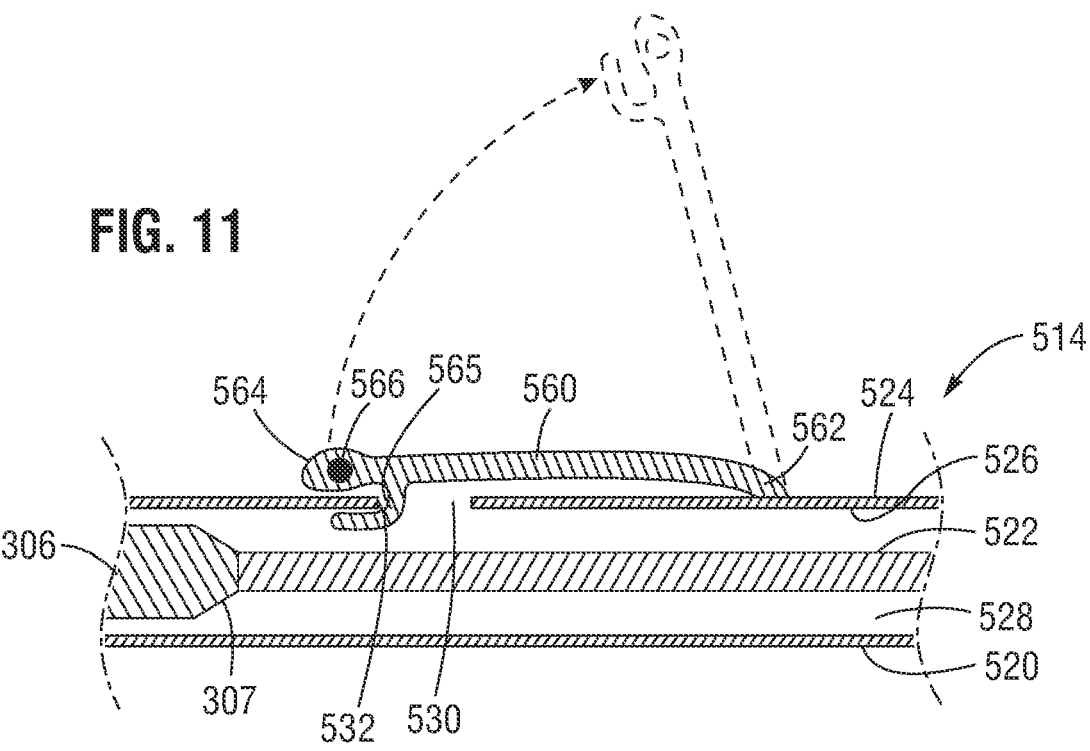
FIG. 11 illustrates a portion of a delivery apparatus having an indicator arm according to a third embodiment.

FIG. 11 shows another embodiment of a retention and actuator assembly 514 that is similar to the retention and actuator assembly 510 described above except for the shape of the indicator arm 560. Specifically, the indicator arm 560 has a first end 562 that is fixedly attached to the outer surface 524 of the support tube 520 and a second end 564 that is configured to be removably attached to the support tube 520 at a location distal to the first end 562. The second end 564 has a hook 565 extending laterally to the indicator arm 560. The indicator arm 560 can be retained in the biased position when the hook 565 extends into the lumen 528 through the aperture 530 and frictionally engages the edge 532 of the aperture 530 and/or the inner surface 526 of the support tube 520 adjacent the aperture 530.

Similarly, during valve expansion, the peripheral portion 307 of the actuator screw (or a different portion of the prosthetic valve or a portion of the delivery apparatus, as described above) can engage the hook 565 inside the lumen 528 and push it out of the lumen 528 through the aperture 530. Thus, the second end 564 can be released from the aperture 530 and the indicator arm 560 can return to its unbiased position.

Similarly, the indicator arm 560 can have a radiopaque marker 566 such that the change of the indicator arm 560 from the biased position to the unbiased position can be visible under fluoroscopy. In some embodiments, the radiopaque marker 566 can be located adjacent the second end 564. In some embodiments, the radiopaque marker 566 can be located on the hook 565. In some embodiments, the radiopaque marker 566 can be located in the middle portion of the indicator arm 560. In alternative embodiments, the entire arm 560 can be formed from a radiopaque material that is visible under fluoroscopy.

Figure 12:
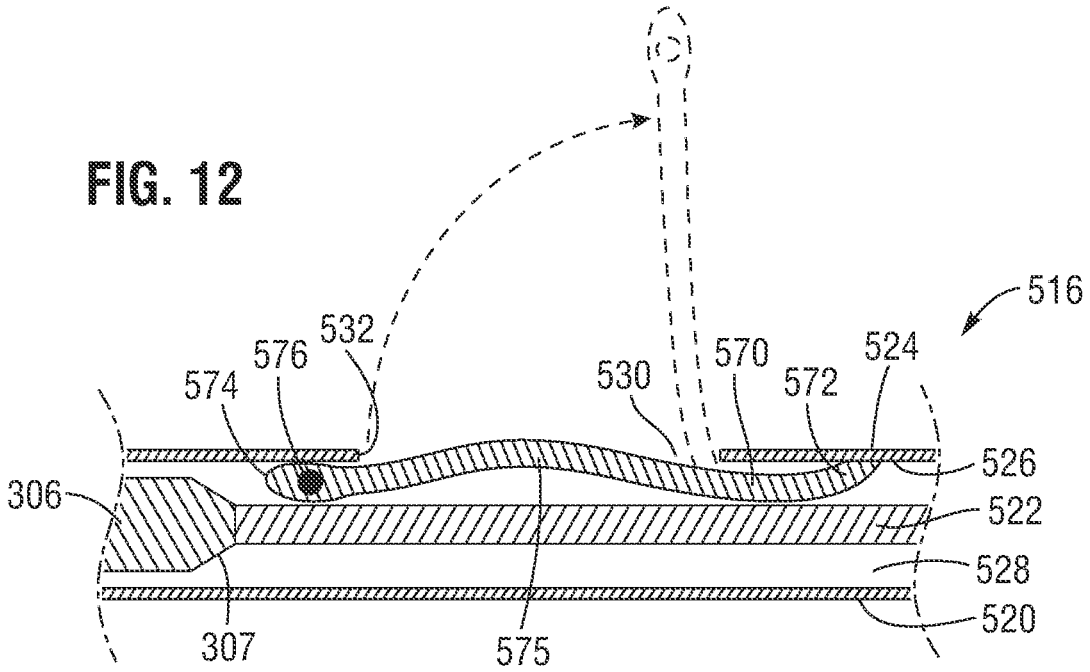
FIG. 12 illustrates a portion of a delivery apparatus having an indicator arm according to a fourth embodiment.

FIG. 12 shows yet another embodiment of a retention and actuator assembly 516 that is similar to the retention and actuator assembly 510 described above except that the indicator arm 570 is located inside the lumen 528 when it is in the biased position. Specifically, the first end 572 of the indicator arm 570 can be fixedly attached to the inner surface 526 of the support tube 520 at a location that is proximal to the aperture 530. The second end 574 of the indicator arm 570 can be configured to be removably attached to the support tube 520 at a location distal to the first end 572. For example, the indicator arm 570 can be retained in the biased position when the second end 574 presses against the inner surface 526 of the support tube 520 at a location that is slightly distal to the aperture 530.

Similarly, during valve expansion, the peripheral portion 307 of the actuator screw (or a different portion of the prosthetic valve or a portion of the delivery apparatus, as described above) can engage the second end 574 inside the lumen 528. A distal portion 575 of the indicator arm 570 adjacent the second end 574 can be made of a flexible material such that it can bend radially outwardly when the second end 574 is pressed in the proximal direction. The aperture 530 can be sized so as to allow the bent distal portion 575 to extend out of the lumen 528 through the aperture 530. Further pressing the second end 574 in the proximal direction can cause the second end 574 to "pop out" of the lumen 528 through the aperture 530, allowing the indicator arm 570 to return to its unbiased position.

Similarly, the indicator arm 570 can have a radiopaque marker 576 such that the change of the indicator arm 570 from the biased position to the unbiased position can be visible under fluoroscopy. In some embodiments, the radiopaque marker 576 can be located adjacent the second end 574. In some embodiments, the radiopaque marker 576 can be located in the middle portion of the indicator arm 570. In alternative embodiments, the entire arm 570 can be formed from a radiopaque material that is visible under fluoroscopy.

More generally, after positioning a prosthetic valve at a target site in a patient's body using a delivery apparatus, an operator can radially expand the prosthetic valve from a radially compressed state to a radially expanded state. The operator can determine that the diameter of the prosthetic valve reaches a predetermined size when the indicator arm changes from a first configuration (e.g., the biased position) to a second configuration (e.g., the unbiased position), and such change can be observed based on differences in location and/or shape between the first and second configurations. As noted above, such observation can be facilitated by a radiopaque marker located on the indicator arm.

In any of the embodiments of FIGS. 9-12, the indicator arm can be biased to the second configuration by a separate biasing element, such as spring (e.g., a torsion spring), connected to the indicator arm and the support tube 520. For example, the indicator arm can be made of a non-elastic material and the biasing element (e.g., spring) can be connected to the indicator arm such that it biases the indicator arm to the second configuration when the second end of the indicator arm is released from the support tube.

Moreover, in alternative embodiments, the first end of the indicator arm (of any of the embodiments describe above) can be connected to the support tube by a hinge, which can include a pin extending through corresponding openings in the first end of the indicator arm and the support tube. Indicator arms with hinges can be self-expanding or can include separate biasing elements.

Furthermore, it should be understood that a delivery apparatus, such as delivery apparatus 100, can include one or more indicator arms as disclosed in FIGS. 9-12 in one or more of the retention and actuator assemblies of the delivery apparatus. In certain embodiments, each retention and actuator assembly of the delivery apparatus has at least one indicator arm as disclosed in any of FIGS. 9-12. In some embodiments, each retention and actuator assembly has the same type of indicator (e.g., each retention and actuator assembly has a respective indicator arm 550). In other embodiments, each retention and actuator assembly has a different indicator arm (e.g., one retention and actuator assembly has an indicator arm 550, while another retention and indicator arm has an indicator arm 570). In some embodiments, the indicator arms in different retention and actuator assemblies can be configured to indicate different expansion sizes of the prosthetic valve. For example, it can be configured such that the prosthetic valve is expanded to a first predetermined size when a first indicator arm in a first retention and actuator assembly changes from its biased position to its unbiased position, and the prosthetic valve is expanded to a second predetermined size when a second indicator arm in a second retention and actuator assembly changes from its biased position to its unbiased position, and so on.

It should be understood that the same concept of using an indicator arm to determine that the diameter of the prosthetic valve is expanded to a predetermined size may be applied when other expansion mechanisms are used (as long as actuating the expansion mechanism can cause the indicator arm to change from one configuration to another configuration that is observable by an operator), such as one or more ratchet mechanisms as described in U.S. Patent Publication No. 2018/0153689, International Application No. PCT/US2019/64373, U.S. Patent Application No. 62/928,291, or U.S. Patent Application No. 62/950,005.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used herein, with reference to the prosthetic valve, delivery apparatus and other components of the delivery assembly, "proximal" refers to a position, direction, or portion of a device that is closer to the handle of the delivery assembly that is outside the patient, while "distal" refers to a position, direction, or portion of a device that is further away from the handle. The terms "longitudinal" and "axial" refer to an axis extending in the proximal and distal directions, unless otherwise expressly defined.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A delivery apparatus configured to provide visual feedback of radial expansion of a prosthetic valve, the delivery apparatus comprising: an indicator arm changeable between a first configuration and a second configuration, the second configuration being different from the first configuration in location or shape of the indicator arm; wherein the indicator arm is configured to remain in the first configuration when a diameter of the prosthetic valve is smaller than a first predetermined size, and change to the second configuration when the diameter of the prosthetic valve is expanded to the first predetermined size.

Example 2. The delivery apparatus of any example herein, particularly example 1, wherein the indicator arm comprises a radiopaque marker such that the change of the indicator arm from the first configuration to the second configuration is visible under fluoroscopy.

Example 3. The delivery apparatus of any example herein, particularly any one of examples 1-2, wherein the indicator arm comprises an elastic material such that the indicator arm in the first configuration is in a biased state and the indicator arm in the second configuration is in an unbiased state.

Example 4. The delivery apparatus of any example herein, particularly any one of examples 1-3, wherein the indicator arm in the first configuration is oriented generally along an axial axis of the prosthetic valve, and the indicator arm in the second configuration is oriented in an oblique angle relative to the axial axis of the prosthetic valve.

Example 5. The delivery apparatus of any example herein, particularly any one of examples 1~4 further comprising a first actuation component and a second actuation component that are configured to interface with an expansion mechanism of the prosthetic valve such that axially moving the second actuation component relative to the first actuation component in a first direction causes the prosthetic valve to expand from a radially compressed state to a radially expanded state, and axially moving the second actuation component relative to the first actuation component in a second direction opposite the first direction causes the prosthetic valve to compress from the radially expanded state to the radially compressed state.

Example 6. The delivery apparatus of any example herein, particularly example 5, wherein the second actuation component extends through a lumen of the first actuation component.

Example 7. The delivery apparatus of any example herein, particularly any one of examples 5-6, wherein a first end of the indicator arm is fixedly attached to a first location of the first actuation component, and a second end of the indicator arm is configured to be removably attached to a second location of the first actuation component when the indicator arm is in the first configuration.

Example 8. The delivery apparatus of any example herein, particularly example 7, wherein the second end of the indicator arm is configured to engage a portion of the expansion mechanism of the prosthetic valve when axially moving the second actuation component relative to the first actuation component in the first direction such that when engaging the portion of the expansion mechanism, the second end of the indicator arm can be released from the second location of the first actuation component.

Example 9. The delivery apparatus of any example herein, particularly example 8, wherein the second location of the first actuation component is so positioned that when the portion of the expansion mechanism of the prosthetic valve engages the second end of the indicator arm, the diameter of the prosthetic valve is expanded to the first predetermined size.

Example 10. The delivery apparatus of any example herein, particularly any one of examples 7-9, wherein the second location is proximal to the prosthetic valve before expanding the prosthetic valve to the first predetermined size, and the first location is proximal to the second location.

Example 11. The delivery apparatus of any example herein, particularly any one of examples 7-10, wherein the first actuation component comprises an aperture at the second location, the aperture being sized to allow the second end of the indicator arm to extend through thereof.

Example 12. The delivery apparatus of any example herein, particularly example 11, wherein the first location is located on an exterior surface of the first actuation component, and the second end of the indicator arm is configured to frictionally engage an edge of the aperture or an interior surface of the first actuation component adjacent the aperture when the indicator arm is in the first configuration.

Example 13. The delivery apparatus of any example herein, particularly example 11, wherein the first location is located on an exterior surface of the first actuation component, and the second end of the indicator arm comprises a hook that is configured to engage an edge of the aperture and an interior surface of the first actuation component adjacent the aperture when the indicator arm is in the first configuration.

Example 14. The delivery apparatus of any example herein, particularly example 11, wherein the first location is located on an interior surface of the first actuation component, and the second end of the indicator arm is configured to press against an interior surface of the first actuation component adjacent the aperture when the indicator arm is in the first configuration.

Example 15. The delivery apparatus of any example herein, particularly any one of examples 7-14, wherein the second end of the indicator arm is configured to be removably attached to at least a third location of the first actuation component when the indicator arm is in the first configuration, the third location being spaced apart from the second location.

Example 16. The delivery apparatus of any example herein, particularly example 15, wherein the second end of the indicator arm is configured to be released from the third location of the first actuation component by the prosthetic valve when axially moving the second actuation component relative to the first actuation component in the first direction, wherein the third location is so configured that when the second end of the indicator arm is released by the prosthetic valve from the third location, the diameter of the prosthetic valve is expanded to a second predetermined size that is different from the first predetermined size.

Example 17. A medical assembly comprising: a prosthetic valve; and a delivery apparatus configured to radially expand and compress the prosthetic valve; wherein the delivery apparatus comprises an indicator arm that is changeable between a first configuration and a second configuration, wherein the indicator arm in the second configuration has a different location or shape than in the first configuration; wherein the indicator arm is configured to remain in the first configuration when a diameter of the prosthetic valve is smaller than a first predetermined size, and change to the second configuration when the diameter of the prosthetic valve is expanded to the first predetermined size.

Example 18. The assembly of any example herein, particularly example 17, wherein the indicator arm comprises an elastic material such that the indicator arm in the first configuration is in a biased state and the indicator arm in the second configuration is in an unbiased state.

Example 19. The assembly of any example herein, particularly any one of examples 17-18, wherein the delivery apparatus comprises a first actuation component and a second actuation component that are configured to interface with an expansion mechanism of the prosthetic valve such that axially moving the second actuation component relative to the first actuation component causes radial expansion or compression of the prosthetic valve.

Example 20. The assembly of any example herein, particularly example 19, wherein the second actuation component extends through a lumen of the first actuation component.

Example 21. The assembly of any example herein, particularly any one of examples 19-20, wherein a first end of the indicator arm is fixedly attached to a first location of the first actuation component, and a second end of the indicator arm is configured to be removably attached to a second location of the first actuation component when the indicator arm is in the first configuration.

Example 22. The assembly of any example herein, particularly any one of examples 19-21, wherein the indicator arm in the second configuration is oriented in an oblique angle relative to an axial axis of the first actuation component.

Example 23. The assembly of any example herein, particularly any one of examples 21-22, wherein the indicator arm comprises a radiopaque marker located adjacent the second end.

Example 24. The assembly of any example herein, particularly any one of examples 21-23, wherein the second end of the indicator arm is configured to engage a portion of the prosthetic valve when axially moving the second actuation component relative to the first actuation component such that when engaging the portion of the prosthetic valve, the second end of the indicator arm can be released from the second location of the first actuation component.

Example 25. The assembly of any example herein, particularly example 24, wherein the second location of the first actuation component is so positioned that when the portion of the prosthetic valve engages the second end of the indicator arm, the diameter of the prosthetic valve is expanded to the first predetermined size.

Example 26. The assembly of any example herein, particularly any one of examples 21-25, wherein the second location is proximal to the prosthetic valve before expanding the prosthetic valve to the first predetermined size, and the first location is proximal to the second location.

Example 27. The assembly of any example herein, particularly any one of examples 21-26, wherein the first actuation component comprises an aperture at the second location, the aperture being sized to allow the second end of the indicator arm to extend through thereof.

Example 28. The assembly of any example herein, particularly example 27, wherein the first location is located on an exterior surface of the first actuation component, and the second end of the indicator arm is configured to frictionally engage an edge of the aperture or an interior surface of the first actuation component adjacent the aperture when the indicator arm is in the first configuration.

Example 29. The assembly of any example herein, particularly example 27, wherein the first location is located on an exterior surface of the first actuation component, and the second end of the indicator arm comprises a hook that is configured to engage an edge of the aperture and an interior surface of the first actuation component adjacent the aperture when the indicator arm is in the first configuration.

Example 30. The assembly of any example herein, particularly example 27, wherein the first location is located on an interior surface of the first actuation component, and the second end of the indicator arm is configured to press against an interior surface of the first actuation component adjacent the aperture when the indicator arm is in the first configuration.

Example 31. The assembly of any example herein, particularly any one of examples 21-30, wherein the second end of the indicator arm is configured to be removably attached to at least a third location of the first actuation component when the indicator arm is in the first configuration, the third location being spaced apart from the second location.

Example 32. The assembly of any example herein, particularly example 31, wherein the second end of the indicator arm is configured to be released from the third location of the first actuation component by the prosthetic valve when axially moving the second actuation component relative to the first actuation component in a proximal direction, wherein the third location is so configured that when the second end of the indicator arm is released by the prosthetic valve from the third location, the diameter of the prosthetic valve is expanded to a second predetermined size that is different from the first predetermined size.

Example 33. A method of implanting a prosthetic valve, the method comprising: positioning a prosthetic valve at a target site in a patient's body using a delivery apparatus, the delivery apparatus comprising an indicator arm which is retained in a first configuration; radially expanding the prosthetic valve from a radially compressed state to a radially expanded state; and determining that a diameter of the prosthetic valve reaches a predetermined size when the indicator arm is changed to a second configuration, wherein the indicator arm in the second configuration has a different location or shape than in the first configuration.

Example 34. The method of any example herein, particularly example 33, wherein the indicator arm comprises an elastic material such that the indicator arm in the first configuration is in a biased state and the indicator arm in the second configuration is in an unbiased state.

Example 35. The method of any example herein, particularly any one of examples 33-34, wherein expanding the prosthetic valve comprises actuating first and second actuation components of the delivery apparatus which are coupled to an expansion mechanism of the prosthetic valve, whereby actuating the first and second actuation components is effective to actuate the expansion mechanism and produce expansion of the prosthetic valve.

Example 36. The method of any example herein, particularly example 35, wherein actuating the first and second actuation components comprises axially moving the second actuation component relative to the first actuation component so as to cause an inner member of the expansion mechanism to move axially relative to an outer member of the expansion mechanism.

Example 37. The method of any example herein, particularly any one of examples 33-36, wherein in the first configuration, a first end of the indicator arm is fixedly attached to a first location of the first actuation component and a second end of the indicator arm is removably attached to a second location of the first actuation component.

Example 38. The method of any example herein, particularly example 37, wherein actuating the expansion mechanism comprises releasing the second end of the indicator arm from the second location of the first actuation component so that the indicator arm changes to the second configuration.

Example 39. The method of any example herein, particularly example 38, wherein releasing the second end of the indicator arm comprises pressing a portion of the prosthetic valve against the second end.

Example 40. The method of any example herein, particularly any one of examples 33-39, wherein the indicator arm comprises a radiopaque marker such that change of the indicator arm from the first configuration to the second configuration can be visualized under fluoroscopy.

Example 41. A delivery apparatus configured to provide visual feedback of radial expansion of a prosthetic valve, the delivery apparatus comprising: an indicator arm moveable between a biased position and an unbiased position; wherein the indicator arm is configured to remain in the biased position when a diameter of the prosthetic valve is smaller than a first predetermined size, and move to the unbiased position when the diameter of the prosthetic valve is expanded to the first predetermined size.

Example 42. The delivery apparatus of any example herein, particularly example 41, wherein the indicator arm comprises a radiopaque marker such that movement of the indicator arm from the biased position to the unbiased position is visible under fluoroscopy.

Example 43. The delivery apparatus of any example herein, particularly any one of examples 41-42 further comprising a first actuation component and a second actuation component that are configured to interface with an expansion mechanism of the prosthetic valve such that axially moving the second actuation component relative to the first actuation component causes radial expansion or compression of the prosthetic valve.

Example 44. The delivery apparatus of any example herein, particularly example 43, wherein the second actuation component extends through a lumen of the first actuation component.

Example 45. The delivery apparatus of any example herein, particularly any one of examples 41-44, wherein a first end of the indicator arm is fixedly attached to a first location of the first actuation component, and a second end of the indicator arm is configured to be removably attached to a second location of the first actuation component when the indicator arm is in the biased position.

Example 46. The delivery apparatus of any example herein, particularly any one of examples 43-45, wherein the indicator arm in the unbiased position is oriented in an oblique angle relative to an axial axis of the first actuation component.

Example 47. The delivery apparatus of any example herein, particularly any one of examples 45-46, wherein the indicator arm comprises a radiopaque marker located adjacent the second end.

Example 48. The delivery apparatus of any example herein, particularly any one of examples 45-47, wherein the second end of the indicator arm is configured to engage a portion of the prosthetic valve when axially moving the second actuation component relative to the first actuation component such that when engaging the portion of the prosthetic valve, the second end of the indicator arm can be released from the second location of the first actuation component.

Example 49. The delivery apparatus of any example herein, particularly example 48, wherein the second location of the first actuation component is so positioned that when the portion of the prosthetic valve engages the second end of the indicator arm, the diameter of the prosthetic valve is expanded to the predetermined size.

Example 50. The delivery apparatus of any example herein, particularly any one of examples 45-49, wherein the second location is proximal to the prosthetic valve before expanding the prosthetic valve to the first predetermined size, and the first location is proximal to the second location.

Example 51. The delivery apparatus of any example herein, particularly any one of examples 45-50, wherein the first actuation component comprises an aperture at the second location, the aperture being sized to allow the second end of the indicator arm to extend through thereof.

Example 52. The delivery apparatus of any example herein, particularly example 51, wherein the first location is located on an exterior surface of the first actuation component, and the second end of the indicator arm is configured to frictionally engage an edge of the aperture or an interior surface of the first actuation component adjacent the aperture when the indicator arm is in the biased position.

Example 53. The delivery apparatus of any example herein, particularly example 51, wherein the first location is located on an exterior surface of the first actuation component, and the second end of the indicator arm comprises a hook that is configured to engage an edge of the aperture when the indicator arm is in the biased position.

Example 54. The delivery apparatus of any example herein, particularly example 51, wherein the first location is located on an interior surface of the first actuation component, and the second end of the indicator arm is configured to press against an interior surface of the first actuation component adjacent the aperture when the indicator arm is in the biased position.

Example 55. The delivery apparatus of any example herein, particularly any one of examples 45-54, wherein the second end of the indicator arm is configured to be removably attached to at least a third location of the first actuation component when the indicator arm is in the biased position, the third location being spaced apart from the second location.

Example 56. The delivery apparatus of any example herein, particularly example 55, the second end of the indicator arm is configured to be released from the third location of the first actuation component by the prosthetic valve when axially moving the second actuation component relative to the first actuation component, wherein the third location is so configured that when the second end of the indicator arm is released by the prosthetic valve from the third location, the diameter of the prosthetic valve is expanded to a second predetermined size that is different from the first predetermined size.

Example 57. A medical assembly comprising: a prosthetic valve; and a delivery apparatus; wherein the delivery apparatus comprises an actuation member and an indicator arm attached to the actuation member; wherein the actuation member is detachably attached to an expansion mechanism of the prosthetic valve, the expansion mechanism being configured to radially expand and compress the prosthetic valve; wherein the indicator arm is changeable between a first configuration and a second configuration, wherein the indicator arm in the second configuration has a different location or shape than in the first configuration; wherein the indicator arm is configured to remain in the first configuration when a diameter of the prosthetic valve is smaller than a first predetermined size, and change to the second configuration when the diameter of the prosthetic valve is expanded to the first predetermined size.

Example 58. The assembly of any example herein, particularly example 57, wherein the indicator arm comprises an elastic material such that the indicator arm in the first configuration is in a biased state and the indicator arm in the second configuration is in an unbiased state.

Example 59. The assembly of any example herein, particularly any one of examples 57-58, wherein the actuation member comprises a first actuation component and a second actuation component that are configured to interface with the expansion mechanism of the prosthetic valve such that axially moving the second actuation component relative to the first actuation component causes radial expansion or compression of the prosthetic valve.

Example 60. The assembly of any example herein, particularly example 59, wherein the second actuation component extends through a lumen of the first actuation component.

Example 61. The assembly of any example herein, particularly any one of examples 59-60, wherein a first end of the indicator arm is fixedly attached to a first location of the first actuation component, and a second end of the indicator arm is configured to be removably attached to a second location of the first actuation component when the indicator arm is in the first configuration.

Example 62. The assembly of any example herein, particularly any one of examples 59-61, wherein the indicator arm in the second configuration is oriented in an oblique angle relative to an axial axis of the first actuation component.

Example 63. The assembly of any example herein, particularly any one of examples 61-62, wherein the indicator arm comprises a radiopaque marker located adjacent the second end.

Example 64. The assembly of any example herein, particularly any one of examples 61-63, wherein the second end of the indicator arm is configured to engage a portion of the prosthetic valve when axially moving the second actuation component relative to the first actuation component such that when engaging the portion of the prosthetic valve, the second end of the indicator arm can be released from the second location of the first actuation component.

Example 65. The assembly of any example herein, particularly example 64, wherein the second location of the first actuation component is so positioned that when the portion of the prosthetic valve engages the second end of the indicator arm, the diameter of the prosthetic valve is expanded to the first predetermined size.

Example 66. The assembly of any example herein, particularly any one of examples 61-65, wherein the second location is proximal to the prosthetic valve before expanding the prosthetic valve to the first predetermined size, and the first location is proximal to the second location.

Example 67. The assembly of any example herein, particularly any one of examples 61-66, wherein the first actuation component comprises an aperture at the second location, the aperture being sized to allow the second end of the indicator arm to extend through thereof.

Example 68. The assembly of any example herein, particularly example 67, wherein the first location is located on an exterior surface of the first actuation component, and the second end of the indicator arm is configured to frictionally engage an edge of the aperture or an interior surface of the first actuation component adjacent the aperture when the indicator arm is in the first configuration.

Example 69. The assembly of any example herein, particularly example 67, wherein the first location is located on an exterior surface of the first actuation component, and the second end of the indicator arm comprises a hook that is configured to engage an edge of the aperture when the indicator arm is in the first configuration.

Example 70. The assembly of any example herein, particularly example 67, wherein the first location is located on an interior surface of the first actuation component, and the second end of the indicator arm is configured to press against an interior surface of the first actuation component adjacent the aperture when the indicator arm is in the first configuration.

Example 71. The assembly of any example herein, particularly any one of examples 61-70, wherein the second end of the indicator arm is configured to be removably attached to at least a third location of the first actuation component when the indicator arm is in the first configuration, the third location being spaced apart from the second location.

Example 72. The assembly of any example herein, particularly example 71, wherein the second end of the indicator arm is configured to be released from the third location of the first actuation component by the prosthetic valve when axially moving the second actuation component relative to the first actuation component in a proximal direction, wherein the third location is so configured that when the second end of the indicator arm is released by the prosthetic valve from the third location, the diameter of the prosthetic valve is expanded to a second predetermined size that is different from the first predetermined size.

Example 73. A method of providing a visual feedback on radial expansion of a prosthetic valve, the method comprising: connecting an actuation member to an expansion mechanism of the prosthetic valve, wherein the actuation member comprises an indicator arm retained in a first configuration; actuating the expansion mechanism with the actuation member to radially expand the prosthetic valve from a radially compressed state to a radially expanded state; and determining that a diameter of the prosthetic valve reaches a predetermined size when the indicator arm is changed to a second configuration, wherein the indicator arm in the second configuration has a different location or shape than in the first configuration.

Example 74. The method of any example herein, particularly example 73, wherein the indicator arm comprises an elastic material such that the indicator arm in the first configuration is in a biased state and the indicator arm in the second configuration is in an unbiased state.

Example 75. The method of any example herein, particularly any one of examples 73-74, wherein the actuation member comprises a first actuation component and a second actuation component, wherein the second actuation component extends through a lumen of the first actuation component.

Example 76. The method of any example herein, particularly example 75, wherein actuating the expansion mechanism comprises axially moving the second actuation component relative to the first actuation component so as to cause an inner member of the expansion mechanism to move axially relative to an outer member of the expansion mechanism.

Example 77. The method of any example herein, particularly any one of examples 73-76, wherein in the first configuration, a first end of the indicator arm is fixedly attached to a first location of the first actuation component and a second end of the indicator arm is removably attached to a second location of the first actuation component.

Example 78. The method of any example herein, particularly example 77, wherein actuating the expansion mechanism comprises releasing the second end of the indicator arm from the second location of the first actuation component so that the indicator arm changes to the second configuration.

Example 79. The method of any example herein, particularly example 78, wherein releasing the second end of the indicator arm comprises pressing a portion of the prosthetic valve against the second end.

Example 80. The method of any example herein, particularly any one of examples 73-79, wherein the indicator arm comprises a radiopaque marker such that change of the indicator arm from the first configuration to the second configuration can be visualized under fluoroscopy.

Exemplary Alternatives

In view of the many possible examples to which the principles of the disclosed technology may be applied, it should be recognized that the illustrated examples are only preferred examples of the technology and should not be taken as limiting the scope of the disclosure. Rather, the scope of the claimed subject matter is defined by the following claims and their equivalents.

The invention claimed is:

1. A delivery apparatus configured to provide visual feedback of radial expansion of a prosthetic valve, the delivery apparatus comprising:

an indicator arm changeable between a first configuration and a second configuration, the second configuration being different from the first configuration in location or shape of the indicator arm;

wherein the indicator arm is configured to remain in the first configuration when a diameter of the prosthetic valve is smaller than a first predetermined size, and change to the second configuration when the diameter of the prosthetic valve is expanded to the first predetermined size; and a first actuation component and a second actuation component that are configured to interface with an expansion mechanism of the prosthetic valve such that axially moving the second actuation component relative to the first actuation component in a first direction causes the prosthetic valve to expand from a radially compressed state to a radially expanded state, and axially moving the second actuation component relative to the first actuation component in a second direction opposite the first direction causes the prosthetic valve to compress from the radially expanded state to the radially compressed state.

2. The delivery apparatus of claim 1, wherein the indicator arm comprises an elastic material such that the indicator arm in the first configuration is in a biased state and the indicator arm in the second configuration is in an unbiased state.

3. The delivery apparatus of claim 1, wherein the indicator arm in the first configuration is oriented generally along an axial axis of the prosthetic valve, and the indicator arm in the second configuration is oriented in an oblique angle relative to the axial axis of the prosthetic valve.

4. The delivery apparatus of claim 1, wherein a first end of the indicator arm is fixedly attached to a first location of the first actuation component, and a second end of the indicator arm is configured to be removably attached to a second location of the first actuation component when the indicator arm is in the first configuration.

5. The delivery apparatus of claim 4, wherein the second end of the indicator arm is configured to engage a portion of the expansion mechanism of the prosthetic valve when axially moving the second actuation component relative to the first actuation component in the first direction such that when engaging the portion of the expansion mechanism, the second end of the indicator arm can be released from the second location of the first actuation component.

6. The delivery apparatus of claim 5, wherein the second location of the first actuation component is so positioned that when the portion of the expansion mechanism of the prosthetic valve engages the second end of the indicator arm, the diameter of the prosthetic valve is expanded to the first predetermined size.

7. The delivery apparatus of claim 4, wherein the first actuation component comprises an aperture at the second location, the aperture being sized to allow the second end of the indicator arm to extend through thereof.

8. The delivery apparatus of claim 7, wherein the first location is located on an exterior surface of the first actuation component, and the second end of the indicator arm is configured to frictionally engage an edge of the aperture or an interior surface of the first actuation component adjacent the aperture when the indicator arm is in the first configuration.

9. The delivery apparatus of claim 7, wherein the first location is located on an exterior surface of the first actuation component, and the second end of the indicator arm comprises a hook that is configured to engage an edge of the aperture and an interior surface of the first actuation component adjacent the aperture when the indicator arm is in the first configuration.

10. The delivery apparatus of claim 7, wherein the first location is located on an interior surface of the first actuation component, and the second end of the indicator arm is configured to press against an interior surface of the first actuation component adjacent the aperture when the indicator arm is in the first configuration.

11. The delivery apparatus of claim 4, wherein the second end of the indicator arm is configured to be removably attached to at least a third location of the first actuation component when the indicator arm is in the first configuration, the third location being spaced apart from the second location.

12. The delivery apparatus of claim 11, wherein the second end of the indicator arm is configured to be released from the third location of the first actuation component by the prosthetic valve when axially moving the second actuation component relative to the first actuation component in the first direction, wherein the third location is so configured that when the second end of the indicator arm is released by the prosthetic valve from the third location, the diameter of the prosthetic valve is expanded to a second predetermined size that is different from the first predetermined size.

13. A delivery apparatus configured to provide visual feedback of radial expansion of a prosthetic valve, the delivery apparatus comprising:

an indicator arm moveable between a biased position and an unbiased position;

wherein the indicator arm is configured to remain in the biased position when a diameter of the prosthetic valve is smaller than a first predetermined size, and move to the unbiased position when the diameter of the prosthetic valve is expanded to the first predetermined size; and a first actuation component and a second actuation component that are configured to interface with an expansion mechanism of the prosthetic valve such that axially moving the second actuation component relative to the first actuation component causes radial expansion or compression of the prosthetic valve.

14. The delivery apparatus of claim 13, wherein a first end of the indicator arm is fixedly attached to a first location of the first actuation component, and a second end of the indicator arm is configured to be removably attached to a second location of the first actuation component when the indicator arm is in the biased position.

15. The delivery apparatus of claim 14, wherein the second end of the indicator arm is configured to engage a portion of the prosthetic valve when axially moving the second actuation component relative to the first actuation component such that when engaging the portion of the prosthetic valve, the second end of the indicator arm can be released from the second location of the first actuation component.

16. The delivery apparatus of claim 15, wherein the second location of the first actuation component is so positioned that when the portion of the prosthetic valve engages the second end of the indicator arm, the diameter of the prosthetic valve is expanded to the predetermined size.

17. The delivery apparatus of claim 14, wherein the first actuation component comprises an aperture at the second location, the aperture being sized to allow the second end of the indicator arm to extend through thereof.

18. The delivery apparatus of claim 17, wherein the first location is located on an interior surface of the first actuation component, and the second end of the indicator arm is configured to press against an interior surface of the first actuation component adjacent the aperture when the indicator arm is in the biased position.

* * * * *